(12) United States Patent
Chodorowski-Kimmes et al.

(10) Patent No.: US 9,561,390 B2
(45) Date of Patent: Feb. 7, 2017

(54) COSMETIC COMPOSITION COMPRISING A SUPRAMOLECULAR POLYMER AND METHOD FOR MAKING UP THE SKIN AND/OR LIPS EMPLOYING A COMPOSITION COMPRISING A SUPRAMOLECULAR POLYMER

(75) Inventors: Sandrine Chodorowski-Kimmes, Senlis (FR); Pascal Arnaud, L'Hay les Roses (FR); Claudia Barba, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/624,741

(22) Filed: Nov. 24, 2009

(65) Prior Publication Data

US 2010/0158832 A1 Jun. 24, 2010

Related U.S. Application Data

(60) Provisional application No. 61/119,207, filed on Dec. 2, 2008.

(30) Foreign Application Priority Data

Nov. 24, 2008 (FR) ..................... 08 57939

(51) Int. Cl.
*A61Q 1/02* (2006.01)
*A61Q 1/06* (2006.01)
*A61K 8/81* (2006.01)

(52) U.S. Cl.
CPC ............... *A61Q 1/02* (2013.01); *A61K 8/8194* (2013.01); *A61Q 1/06* (2013.01)

(58) Field of Classification Search
CPC ........... A61Q 1/02; A61Q 1/06; A61K 8/8194
See application file for complete search history.

(56) References Cited

U.S. PATENT DOCUMENTS

| | | | |
|---|---|---|---|
| 6,395,262 B1 * | 5/2002 | Favre et al. .................. 424/61 |
| 6,572,729 B1 | 6/2003 | Auvray et al. |
| 2001/0053377 A1 | 12/2001 | Mondet et al. |
| 2003/0017182 A1 | 1/2003 | Tournilhac |
| 2004/0161394 A1 | 8/2004 | Mougin et al. |
| 2005/0031566 A1 * | 2/2005 | Cooper et al. ............. 424/70.11 |
| 2007/0093619 A1 * | 4/2007 | Bui et al. ..................... 525/477 |
| 2007/0189991 A1 | 8/2007 | Mougin et al. |
| 2008/0127429 A1 | 6/2008 | Brun et al. |
| 2009/0130028 A1 | 5/2009 | Rollat-Corvol et al. |

FOREIGN PATENT DOCUMENTS

| | | |
|---|---|---|
| EP | 1 155 687 A1 | 11/2001 |
| EP | 13110533 A2 * | 5/2003 |
| EP | 1 392 222 B1 | 3/2004 |
| EP | 1 435 900 B1 | 7/2004 |
| EP | 1 797 868 A1 | 6/2007 |
| EP | 1 944 064 A2 | 7/2008 |
| FR | 2 741 530 A1 | 5/1997 |
| FR | 2 782 723 A1 | 3/2000 |
| FR | 2 816 503 A1 | 5/2002 |
| FR | 2 825 628 A1 | 12/2002 |
| FR | 2 907 674 A1 | 5/2008 |
| FR | 2 907 678 A1 | 5/2008 |
| WO | WO 02/098377 A1 | 12/2002 |
| WO | WO 03/032929 A2 | 4/2003 |
| WO | WO 2005/042641 A1 | 5/2005 |
| WO | WO 2007/039832 A2 | 4/2007 |

OTHER PUBLICATIONS

Folmar et al., Cooperative Dynamics in Duplexes of Stacked Hydrogen-Bonded Moieties, J. Am. Chem. Soc. 1999, 121, 9001-9007.*
Brigitte J.B. Folmer et al., "Supramolecular Polymer Materials: Chain Extension of Telechetic Polymers Using a Reactive Hydrogen-Bonding Synthon," Advanced Materials, vol. 12, No. 12, pp. 874-878, 2000.
Database Biosis [Online], Biosciences Information Service, Ikkala Olli et al, "Functional Materials Based on Self-assembly of Polymeric Supramolecules," Mar. 29, 2002, XP002538770.
French Search Report for FR 0857939, dated Oct. 29, 2009.
French Search Report for FR 0857936, dated Jul. 27, 2009.
English language abstract of FR 2 907 674 A1, May 2, 2008.

* cited by examiner

Primary Examiner — Trevor Love
(74) Attorney, Agent, or Firm — Polsinelli PC

(57) ABSTRACT

The present disclosure relates to a method for making up the skin and/or lips, wherein a cosmetic makeup composition comprising, in a cosmetically acceptable medium, at least one polyalkene-based supramolecular polymer is applied. The disclosure also relates to a cosmetic composition for making up the skin and/or lips, comprising, in a cosmetically acceptable medium, at least one polyalkene-based supramolecular polymer and at least one coloring material.

25 Claims, No Drawings

COSMETIC COMPOSITION COMPRISING A SUPRAMOLECULAR POLYMER AND METHOD FOR MAKING UP THE SKIN AND/OR LIPS EMPLOYING A COMPOSITION COMPRISING A SUPRAMOLECULAR POLYMER

This application claims benefit of U.S. Provisional Application No. 61/119,207, filed Dec. 2, 2008, the contents of which are incorporated herein by reference. This application also claims benefit of priority under 35 U.S.C. §119 to French Patent Application No. FR 0857939, filed Nov. 24, 2008, the contents of which are also incorporated herein by reference.

The present disclosure relates to a composition for making up the skin, for example the face, or the lips, comprising at least one polyalkene-based supramolecular polymer. The disclosure also relates to a method for making up the skin and/or lips comprising the application of such a composition.

When consumers use a product for the complexion, such as a foundation, they want this product to exhibit, after application, good hold on the skin and for example, they do not want it to transfer onto clothes.

It is known to a person skilled in the art to use polymers in order to obtain these properties of lengthy hold during the day. These polymers have very different chemical natures and are generally carried either in a fatty phase or an aqueous phase. Mention may be made, as examples of silicone resins, polyacrylates and latexes. While these polymers may indeed contribute hold properties, such as transfer-free properties, these properties may be accompanied by discomfort, for example during the application of the product (difficult spreading, stickiness) and/or during the day (tightness, mask effect).

In the field of lipsticks, good hold of the composition is also a requirement of consumers. It is generally obtained by using "film-forming" polymers, so as to limit color transfer. The production of polymer films on the lips can, however, be a source of discomfort, for instance due to the tightening effects which the film-forming polymer exerts on the labial mucous membrane.

Furthermore, makeup compositions for the lips are frequently glossy or exhibit a glossy effect. This glossiness, which makes it possible to enhance the lips, is generally obtained by the formation of glossy oils and/or of particles possessing glints. However, the use of glossy oils may generate stickiness, this sticky nature resulting in these compositions leaving traces on substrates, such as glasses or coffee cups, and thus transferring.

The need thus remains to have available polymers capable of being employed in making up the complexion which make it possible to simultaneously obtain good hold properties while retaining a certain comfort on use.

The need also remains to have available polymers capable of being employed in making up the lips which make it possible to simultaneously obtain a deposited layer which is comfortable, glossy and free from transfer.

One aim of the present disclosure is to provide such polymers.

Accordingly, one aspect of the disclosure is a method for making up the skin and/or lips, wherein a cosmetic makeup composition comprising, in a cosmetically acceptable medium, at least one polyalkene-based supramolecular polymer is applied to the skin and/or lips.

Another aspect of the disclosure is a cosmetic composition for making up the skin and/or lips, comprising, in a cosmetically acceptable medium, at least one polyalkene-based supramolecular polymer and at least one coloring material.

"Supramolecular" polymers are known generally in cosmetics.

The cosmetic compositions according to the disclosure thus comprise at least one polyalkene-based supramolecular polymer.

As used herein, polyalkene-based supramolecular polymer is understood to mean a polymer resulting from the reaction, for example from the condensation, of at least one polyalkene polymer, functionalized by at least one reactive group, with at least one joining group, functionalized by at least one reactive group capable of reacting with the reactive group or groups of the at least one functionalized polyalkene polymer, the at least one joining group being capable of forming at least three H (hydrogen) bonds, for example at least four H bonds. In at least one embodiment the at least one joining group is capable of forming at least four H bonds.

The supramolecular polymer according to the disclosure is capable of forming a supramolecular polymer chain or network by (self)assembling of the said polymer according to the disclosure with at least one other identical or different polymer, each "assembling" involving at least one pair of identical or different matched joining groups carried by each of the polymers according to the disclosure.

As used herein, the term joining group is understood to mean any group which comprises groups which donate or accept H bonds and which is capable of establishing at least three H bonds, such as at least four H bonds, with an identical or different partner joining group. These joining groups can be lateral to the polymer backbone (in a side branch) and/or carried by the ends of the polymer backbone and/or carried in the chain forming the polymer backbone. They can be distributed in a random or controlled fashion.

For example, the at least one functionalized polyalkene polymer capable of forming all or part of the polymer backbone of the supramolecular polymer according to the disclosure is of formula HX—P—X'H, wherein:

XH and X'H are reactive groups with X and X', which are identical or different, chosen from O, SH, NH or $NR_a$, $R_a$ representing a $C_1$-$C_6$ alkyl group; in at least one embodiment, X and/or X' denote O;

P represents a homo- or copolymer capable of being obtained by polymerization of at least one mono- or polyunsaturated and linear, cyclic and/or branched $C_2$-$C_{10}$, such as a $C_2$-$C_4$, alkene; in a further embodiment, P represents a polyethylene, a polybutylene, a polybutadiene, a polyisoprene, a poly(1,3-pentadiene), a polyisobutylene and the copolymers thereof; in another embodiment P represents a poly(ethylene/butylene).

Poly(ethylene/butylene)s are copolymers of 1-butene and ethylene. They can be represented schematically by the sequence of following units:

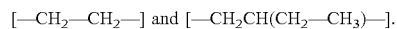

The polybutadienes can be poly(1,4-butadiene)s or poly(1,2-butadiene)s, which can respectively be represented schematically by the sequences of following units:

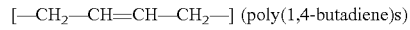

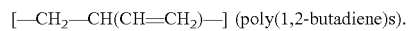

For example, the polybutadienes can be poly(1,2-butadiene)s.

The polyisoprenes can be represented schematically by the sequences of following units:

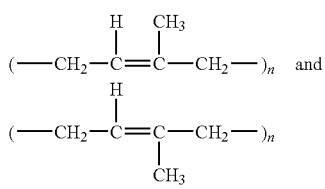

It is possible to also use a mixture of above units, in order to form copolymers.

For example, the at least one functionalized polyalkene polymer exhibits a number-average molecular weight (Mn) of greater than or equal to 1,000, for example ranging from 1,000 to 5,000, or ranging from 1,500 to 3,500.

The at least one functionalized polyalkene polymer can be completely hydrogenated, in order to avoid risks of cross-linking.

The supramolecular polymers can additionally comprise, in their structure, other units resulting from other monomers. Mention may be made, for example, as comonomers, of styrene or epoxy. In at least one embodiment, they do not comprise other units resulting from other monomers and are thus composed solely of polyalkene polymers (100%) to form the polymer backbone.

The at least one polyalkene polymer is functionalized by at least one reactive group, for example functionalized by at least two reactive groups. The functionalization may take place at the end of chains. The reference is then to telechelic polymers. The at least one functionalization group, or reactive group, can be attached to the polyalkene polymer via linkers, such as linear or branched $C_1$-$C_4$ alkylene groups, or directly by a single bond. Mention may be made, for example, as reactive group, of the OH, $NH_2$, NHR, SH or NCO functional groups.

Mention may be made, for example, among functionalized polyalkene polymers, of polydienes, such as hydrogenated polydienes comprising hydroxyl functional groups, for example comprising hydroxyl ends, and polyolefins comprising hydroxyl ends.

Polydienes comprising hydroxyl ends are defined, for example, in FR 2 782 723. They can be chosen from homopolymers and copolymers of butadiene, isoprene and 1,3-pentadiene. In at least one embodiment, they have a number-average molecular weight (Mn) of less than 7,000, for example ranging from 1,000 to 5,000, and exhibit a functionality of hydroxyl ends ranging from 1.8 to 3, for example about 2. Mention may be made, for example, of the hydroxylated polybutadienes sold by Elf Atochem under the POLY BD R-45HT and POLY BD R-20 LM trade names, which may be used hydrogenated, for example, and the dihydroxylated hydrogenated poly(1,2-butadiene)s, such as GI3000 (Mn=3100), GI2000 (Mn=2100) and GI1000 (Mn=1500), sold by Nisso.

Mention may also be made, for example, among polyolefins comprising hydroxyl ends, of polyolefins, which are homopolymers or copolymers, comprising α,ω-hydroxyl ends, such as polyisobutylenes comprising α,ω-hydroxyl ends, and copolymers of formula:

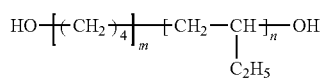

such as those sold by Mitsubishi under the POLYTAIL trade name.

The supramolecular polymers according to the disclosure also have, in their structure, at least one residue of at least one joining group capable of forming at least 3H bonds, for example at least 4H bonds, the at least one joining group being initially functionalized by at least one reactive group.

The at least one reactive group can be attached to the at least one joining group via at least one linker, such as at least one linear or branched $C_1$-$C_4$ alkylene group, or directly by a single bond.

The at least one reactive group has to be capable of reacting with at least one reactive group carried by the at least one functionalized polyalkene of the at least one functionalized polyalkene polymer. Mention may be made, as reactive group, for example, of carboxyl, hydroxyl, amino or isocyanate groups. In one embodiment, the at least one reactive group comprises at least one —N=C=O or —N=C=S group; in a further embodiment, the at least one reactive group comprises an —N=C=O (isocyanate) group.

For example, the at least one linker can be chosen from phenylene, 1,4-nitrophenylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), isophorone, 4,4'-methylenebiscyclohexylene, tolylene, 2-methyl-1,3-phenylene, 4-methyl-1,3-phenylene and 4,4-biphenylenemethylene groups.

In at least one embodiment, the at least one linker is chosen from isophorone, —$(CH_2)_2$—, —$(CH_2)_6$—, —$CH_2CH(CH_3)$—$CH_2$—$C(CH_3)_2$—$CH_2$—$CH_2$—, 4,4'-methylenebiscyclohexylene and 2-methyl-1,3-phenylene groups.

As used herein, "isophorone" is understood to mean the following group:

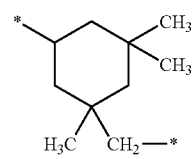

In one embodiment, the at least one functionalized joining group capable of forming at least 3H bonds can comprise at least 3 functional groups, such as at least 4 functional groups, chosen from:

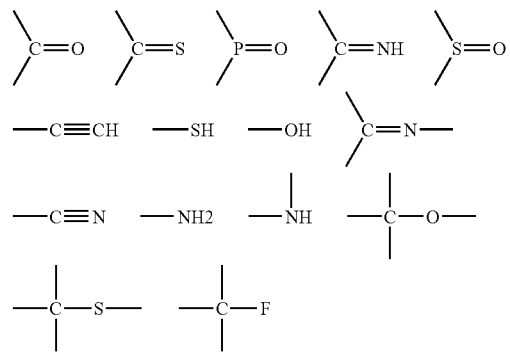

These functional groups can be categorized into two categories:

functional groups which donate H bonds:

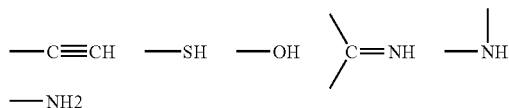

functional groups which accept H bonds:

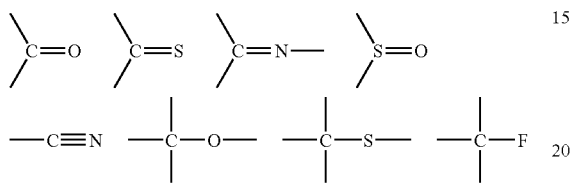

The at least one joining group capable of forming at least 3H bonds forms at least one base structural element comprising at least 3 functional groups, such as at least 4 functional groups, or for example, at least 4 functional groups capable of establishing H bonds. The at least one base structural element capable of establishing H bonds can be represented schematically in the following way:

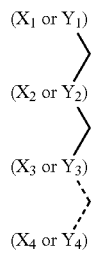

where $X_i$ is a functional group which accepts H bonds and $Y_i$ is a functional group which donates H bonds.

Thus, each structural element must be able to establish H bonds with at least one partner structural element which is/are identical (that is to say, self-complementary) or different, so that each pairing of two partner structural elements takes place by formation of at least three H bonds, for example at least four H bonds.

An acceptor of protons X will be paired with a donor of protons Y. Several possibilities are thus offered, for example pairing of:

XXXX with YYYY;
XXXY with YYYX;
XXYX with YXXY;
XYYX with YXXY;
XXYY with YYXX, which may or may not be self-complementary;
XYXY with YXYX, which may or may not be self-complementary.

In one embodiment, the at least one joining group can establish four H bonds with an identical (or self-complementary) partner group, among which two donor bonds (for example NH) and two acceptor bonds (for example CO and —C=N—).

For example, the joining groups capable of forming at least 3H bonds can be chosen from the following families, it being understood that all the tautomeric forms are included:

(i) aminopyrimidones of formula:

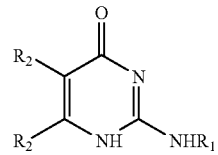

(ii) ureidopyrimidones of formula:

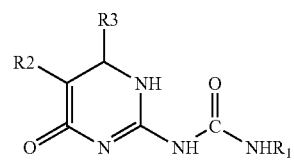

(iii) acylaminopyridines, such as:
monoacylaminopyridines of formula:

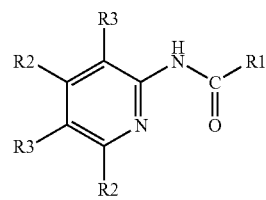

di(acylamino)pyridines, such as 2,6-di(acylamino)pyridines of formula:

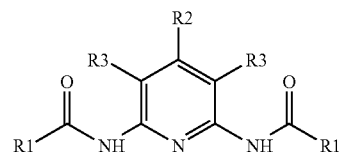

(iv) aminopyrimidines, such as:
the aminopyrimidine compounds of formulae:

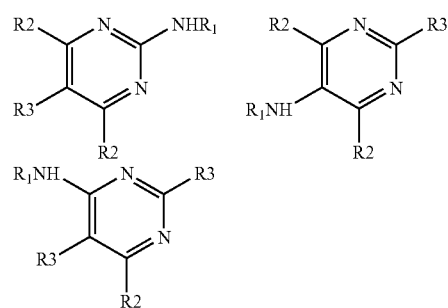

the diaminopyrimidine compounds of formulae:

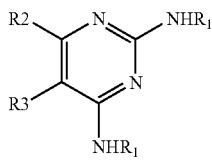 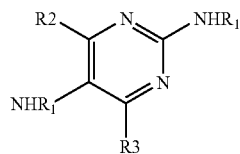

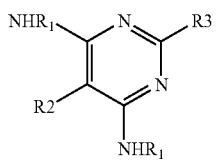 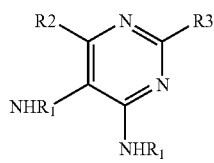

or the triaminopyrimidine compounds;

(v) ureidotriazines, such as mono-, di- and triureidotriazines, for example the ureidoaminotriazines of formula:

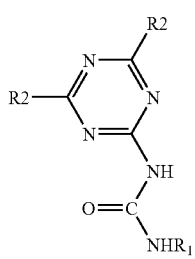

(vi) (acylamino)triazines, such as mono-, di- and triacylaminotriazines, which optionally comprise amino (mono-, di- or triamino), for example:

di(acylamino)triazines of formula:

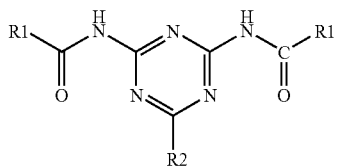

(acylamino)aminotriazines (mono- or diacylamino and mono- or diamino), for example the compounds of formula:

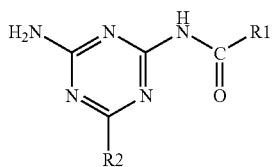

acylaminotriazines of formula:

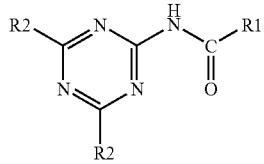

or triacylaminotriazines;
(vii) aminotriazines, such as monoaminotriazines;
2,6-diamino-s-triazines of formula:

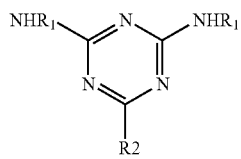

or triamino-s-triazine compounds of formula:

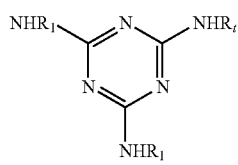

(viii) acylaminotriazoles of formula:

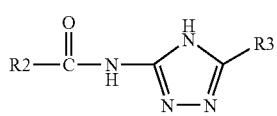

(ix) compounds of the family of urazolylbenzoic acid of formula:

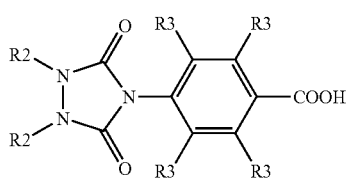

(x) phthalhydrazides of formula:

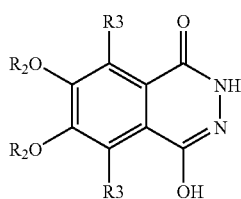

(xi) uracils of formula:

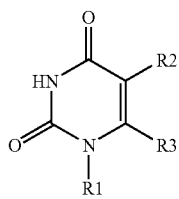

(xii) thymines of formula:

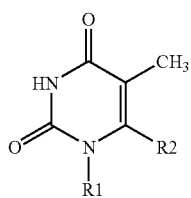

(xiii) succinimides of formula:

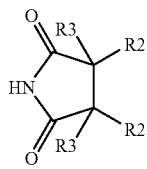

(xiv) glutarimides of formula:

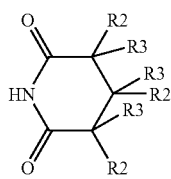

(xv) compounds of the family of cyanuric acid of formula:

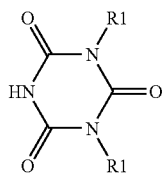

(xvi) maleimides of formula:

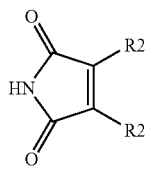

(xvii) compounds of the family of barbituric acid, of formula:

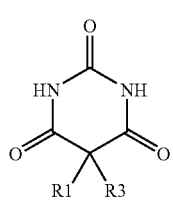

(xviii) compounds of the following formulae:

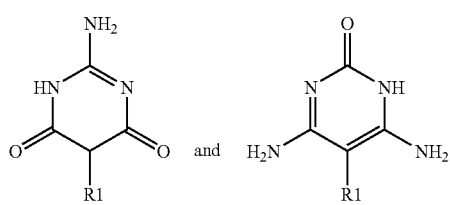

(xix) compounds of the family of trimellitic acid, of formula:

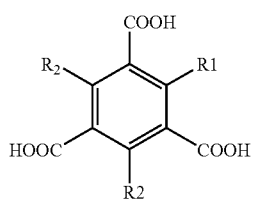

(xx) ureidopyridines, such as mono- or diureidopyridines, for example those of formulae:

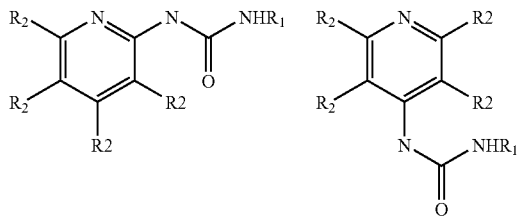

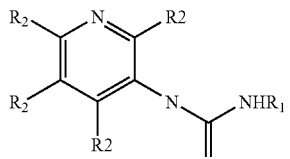

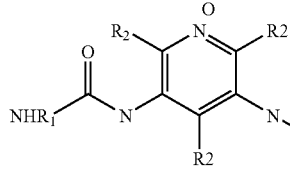

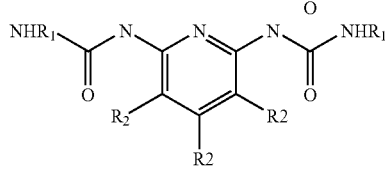

(xxi) carbamoylpyridines of formulae:

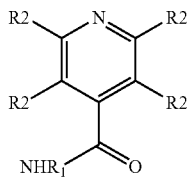
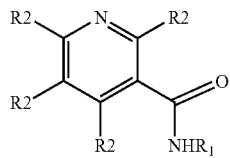
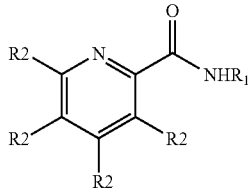

(xxii) adenines of formula:

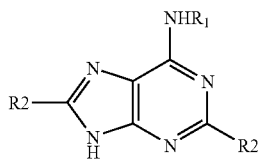

(xxiii) guanines of formula:

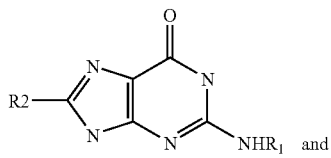

and (xxiv) cytidines of formula:

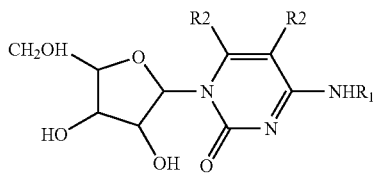

In all the above formulae, the meanings of the radicals are as follows:
(a) the $R_1$ radicals, which are identical or different, represent a single bond, a hydrogen atom, a halogen atom or a saturated or unsaturated, optionally aromatic, linear, branched and/or cyclic monovalent $C_1$-$C_{6000}$ carbon-comprising group (such as at least one alkyl group) optionally comprising at least one heteroatom, such as O, S, N, P, Cl, Br, Cl, Br or F.

In one embodiment, at least one $R_1$ radical is chosen from $C_4$-$C_{12}$ cycloalkyl groups, linear or branched $C_1$—$C_{30}$ alkyl groups and $C_4$-$C_{12}$ aryl groups which are optionally substituted by an amino, ester and/or hydroxyl functional group.

In a further embodiment, $R_1$ is chosen from $C_4H_9$, phenylene, 1,4-nitrophenylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), isophorone, 4,4'-methylenebiscyclohexylene, tolylene, 2-methyl-1,3-phenylene, 4-methyl-1,3-phenylene and 4,4-biphenylenemethylene groups and a single bond. In another embodiment R1 is chosen from isophorone, —$(CH_2)_2$—, —$(CH_2)_6$—, —$CH_2CH(CH_3)$—$CH_2$—$C(CH_3)_2$—$CH_2$—$CH_2$—, 4,4'-methylenebiscyclohexylene or 2-methyl-1,3-phenylene groups and a single bond.

(b) the $R_2$ radicals, which are identical or different, are chosen from single bonds, hydrogen atoms, halogen atoms (for example, —Br, —Cl or —F), —OH radicals, —N(R)$_2$ radicals (for example R being H or a linear and/or branched $C_1$-$C_{12}$, such as $C_1$-$C_4$, alkyl radicals, for example methyl or ethyl radicals) or saturated or unsaturated, optionally aromatic, linear, branched and/or cyclic monovalent $C_1$—$C_{6000}$ hydrocarbon groups optionally comprising at least one heteroatom, such as O, S, N, P or F.

For example, the $R_2$ radicals can be chosen from H, CN, $NH_2$, and the following groups:
$C_1$-$C_{30}$ alkyl groups;
$C_4$-$C_{12}$ cycloalkyl groups;
$C_4$-$C_{12}$ aryl groups;
($C_4$-$C_{12}$)aryl($C_1$-$C_{30}$)alkyl groups;
$C_1$-$C_4$ alkoxy groups;
arylalkoxy groups, such as aryl($C_1$-$C_4$)alkoxy groups;
$C_4$-$C_{12}$ heterocycles;
thioalkoxy groups; and
sulphoxy groups;
or mixtures thereof these groups optionally being substituted by an amino, ester and/or hydroxyl functional group.

In at least one embodiment, $R_2$ is chosen from H, $CH_3$, $C_{13}H_{27}$, $C_7H_{15}$ and phenyl.

(c) the $R_3$ radicals, which are identical or different, are chosen from hydrogen atoms and saturated or unsaturated, optionally aromatic, linear, branched and/or cyclic monovalent $C_1$-$C_{6000}$ hydrocarbon groups optionally comprising at least one heteroatom, such as O, S, N, P or F.

In at least one embodiment, the $R_3$ radical is chosen from $C_4$-$C_{12}$ cycloalkyl groups, linear or branched $C_1$-$C_{30}$ alkyl groups and $C_4$-$C_{12}$ aryl groups which are optionally substituted by an amino, ester and/or hydroxyl functional group, for example a methyl group.

In all these formulae, it is understood that at least one, for example one or two, of the $R_1$ and $R_2$ groups is a single bond constituting the point of attachment of the at least one joining group capable of forming at least three H bonds on the residue of the graft. For example, the point of attachment can be carried by $R_1$ and/or $R_2$, and in at least one embodiment it is carried by $R_1$.

For example, the at least one joining group capable of forming at least three H bonds can be chosen from:
(a) complementary and identical groups, that is to say self-complementary groups, for example:
aminopyrimidones or ureidopyrimidones,
compounds of the family of trimellitic acid or of urazolylbenzoic acid,
acylaminopyridines, ureidopyridines or carbamoylpyridines,
acylaminotriazines, ureidotriazines, such as ureidoaminotriazines, or diaminotriazines,
acylaminotriazoles,
phthalhydrazides, compounds of formulae:

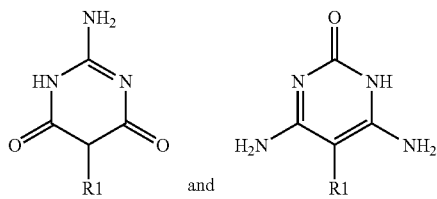

wherein R₁ is chosen from single bonds, hydrogen atoms, and saturated or unsaturated, optionally aromatic, linear, branched and/or cyclic monovalent $C_1$-$C_{6000}$ hydrocarbon groups optionally comprising at least one heteroatom, such as O, S, N, P or F; and
(b) complementary but different groups, for example:
adenine complementary to guanine,
cytidine complementary to thymine,
triamino-s-triazine complementary to uracil or to succinimide or to glutarimide or to cyanuric acid or to thymine or to maleimide or to (di)aminopyrimidine or to barbituric acid,
(acylamino)amino-s-triazine complementary to uracil or to succinimide or to glutarimide or to cyanuric acid or to thymine or to maleimide or to (di)aminopyrimidine or to barbituric acid.

For example, the at least one joining group capable of forming at least three H bonds can be chosen from self-complementary groups, such as those capable of establishing at least four H bonds with themselves. Mention may be made, for example, among these groups, of:
ureidopyrimidones;
ureidopyridines or carbamoylpyridines;
acylamino-s-triazines, such as (acyl)diamino-s-triazines;
ureidotriazines;
phthalhydrazides;
compounds of formulae:

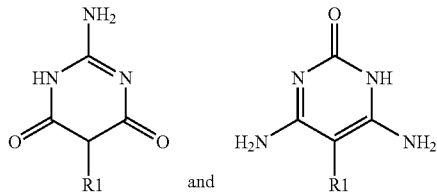

wherein the $R_1$, $R_2$ and $R_3$ radicals have the meanings given above.

Mention may also be made, as joining groups capable of forming at least 3H bonds, of the groups derived from ureidopyrimidones, for example from 2-ureidopyrimidone or from 6-methyl-2-ureidopyrimidone.

Unless specified otherwise, as used herein "joining group" is understood to mean the group without its at least one reactive functional group.

For example, the at least one functionalized joining group capable of reacting with the at least one functionalized polyalkene polymer to give the supramolecular polymer according to the disclosure can be chosen from those of formula:

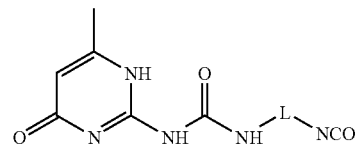

wherein L is a single bond or a saturated or unsaturated, for example aromatic, linear, cyclic and/or branched, divalent $C_1$-$C_{20}$ carbon-comprising (alkylene) group optionally comprising from 1 to 4 N and/or O heteroatoms, for example in the form of an $NO_2$ substituent, such as phenylene, 1,4-nitrophenylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), isophorone, 4,4'-methylenebiscyclohexylene, tolylene, 2-methyl-1,3-phenylene, 4-methyl-1,3-phenylene or 4,4-biphenylenemethylene groups, for example isophorone, —(CH₂)₂—, —(CH₂)₆—, —CH₂CH(CH₃)—CH₂—C(CH₃)₂—CH₂—CH₂—, 4,4'-methylenebiscyclohexylene or 2-methyl-1,3-phenylene groups.

In at least one embodiment, the supramolecular polymer of the disclosure corresponds to the formula:

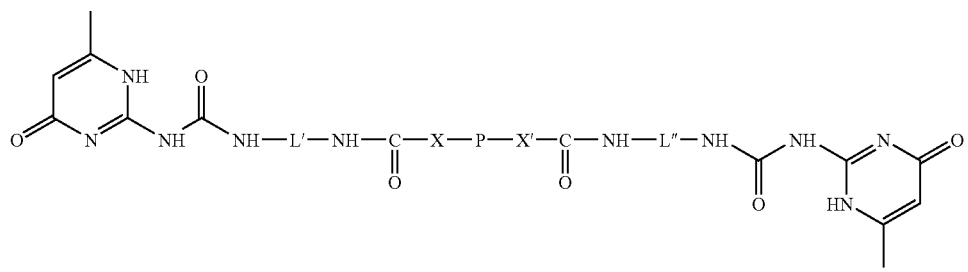

wherein:
L' and L" have, independently of one another, the meanings indicated above for L; and
X, X' and P have the meanings indicated above for the at least one functionalized polyalkene polymer.

In at least one embodiment, X=X'=O.

In another embodiment, L' and L" represent a saturated or unsaturated and linear, cyclic and/or branched divalent $C_1$-$C_{20}$ carbon-comprising (alkylene) group, such as an isophorone, —(CH$_2$)$_2$—, —(CH$_2$)$_6$—, —CH$_2$CH(CH$_3$)—CH$_2$—C(CH$_3$)$_2$—CH$_2$—CH$_2$—, 4,4'-methylenebiscyclohexylene or 2-methyl-1,3-phenylene group.

In a further embodiment, P is chosen from polyethylenes, polybutylenes, polybutadienes, polyisoprenes, poly(1,3-pentadiene)s, polyisobutylenes and a copolymers thereof, such as poly(ethylene/butylene)s.

The polymer according to the disclosure can be prepared by any process normally employed by a person skilled in the art, for example in order to form a urethane bond between the free OH functional groups of a polyalkene and the isocyanate functional groups carried by the at least one joining group.

By way of illustration only, and not by way of limitation, a first general preparation process may comprise:
  optionally making sure that the polymer to be functionalized does not comprise residual water;
  heating the polymer comprising at least one reactive functional group, for example 2 reactive functional groups, such as at least one OH, to a temperature ranging from 60° C. to 140° C., it being possible for the hydroxyl number of the polymer to act as reference in order to measure the state of progression of the reaction;
  adding, for example directly, the at least one joining group carrying the reactive functional groups, such as isocyanate functional groups;
  optionally stirring the mixture, under a controlled atmosphere, at a temperature ranging from 90 to 130° C., for 1 to 24 hours;
  optionally monitoring, by infrared spectroscopy, the disappearance of the band characteristic of the isocyanates (between 2500 and 2800 cm$^{-1}$), so as to halt the reaction at the complete disappearance of the peak, and then allowing the final product to return to ambient temperature.

The reaction can also be monitored by quantitative determinations of the hydroxyl functional groups; it is also possible to add ethanol in order to make sure that the residual isocyanate functional groups have completely disappeared.

The reaction can be carried out in the presence of a solvent, such as methyltetrahydrofuran, tetrahydrofuran, toluene, propylene carbonate or butyl acetate. It is also possible to add a catalyst conventional for the formation of the urethane bond. Mention may be made, as example, of dibutyltin dilaurate. At the end, the polymer can be washed and dried, and optionally purified, according to the general knowledge of a person skilled in the art.

According to a 2$^{nd}$ method of preparation, the reaction can comprise the following stages:
  (i) functionalizing the polymer, for example predried, by a diisocyanate according to the reaction scheme:

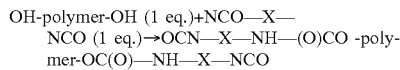

The diisocyanate can optionally be in excess with respect to the polymer. This first stage can be carried out in the presence of solvent, at a temperature ranging from 20° C. to 100° C. This first stage can be followed by a period of stirring, under a controlled atmosphere, for a time ranging from 1 to 24 hours. The mixture can optionally be heated. The state of progression of this first stage can be monitored by quantitative determination of the hydroxyl functional groups.

then
  (ii) reaction of the prepolymer obtained above with 6-methylisocytosine of formula:

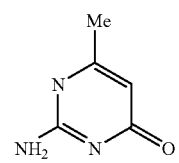

This second stage can optionally be carried out in the presence of a cosolvent, such as toluene, butyl acetate or propylene carbonate. The reaction mixture can be heated at a temperature ranging from 80° C. to 140° C. for a time ranging from 1 to 24 hours. In one embodiment, the presence of a catalyst, such as dibutyltin dilaurate, can promote the production of the desired final product.

The reaction can be monitored by infrared spectroscopy, by monitoring the disappearance of the peak characteristic of the isocyanate between 2200 and 2300 cm$^{-1}$. At the end of the reaction, ethanol can be added to the reaction medium in order to neutralize the possible residual isocyanate functional groups. The reaction mixture can optionally be filtered. The polymer can also be directly stripped in a cosmetic solvent.

The polyalkene-based supramolecular polymer, alone or as a mixture, can be present in the cosmetic makeup composition according to the disclosure in an amount ranging from 0.1 to 70% by weight relative to the total weight of the composition, for example from 0.2 to 40% by weight, or from 0.5 to 15% by weight.

In at least one embodiment, the makeup composition is provided in the form of a foundation and the at least one polyalkene-based supramolecular polymer, can be present therein in a total amount ranging from 0.1 to 10% by weight relative to the total weight of the composition, for example from 0.2 to 5% by weight, or from 0.5 to 3% by weight.

In another embodiment, the makeup composition is provided in the form of a lipstick and the at least one polyalkene-based supramolecular polymer, can be present in a total amount ranging from 0.1 to 70% by weight relative to the total weight of the composition, such as from 0.2 to 40% by weight or from 0.5 to 15% by weight.

In one embodiment, the cosmetic makeup composition according to the disclosure further comprises at least one cosmetically acceptable medium which can comprise the usual ingredients, depending on the destination of the composition.

In one embodiment, the composition for making up the skin and/or lips according to the disclosure comprises at least one coloring material which can be chosen from pigments and water-soluble and fat-soluble dyes.

As used herein, the term "pigment" is understood to mean any pigment contributing color to keratinous substances.

Their solubility in water at 25° C. and at atmospheric pressure (760 mmHg) is less than 0.05% by weight, such as less than 0.01%.

The pigments which can be used include those chosen from organic and inorganic pigments known in the art, for example those which are described in Kirk-Othmer's Encyclopaedia of Chemical Technology and in Ullmann's Encyclopaedia of Industrial Chemistry.

These pigments can be provided in the form of a powder or of a pigment paste. They can be coated or uncoated.

The pigments can, for example, be chosen from inorganic pigments, organic pigments, lakes, special effect pigments, such as pearlescent agents or glitter, and mixtures thereof.

The pigment can be an inorganic pigment. As used herein, "inorganic pigment" is understood to mean any pigment which corresponds to the definition of Ullmann's Encyclopaedia in the "Inorganic Pigment" chapter. Mention may be made, for example, among inorganic pigments of use in the present disclosure, of iron or chromium oxides, manganese violet, ultramarine blue, chromium hydrate, ferric blue and titanium oxide.

The pigment can be an organic pigment. As used herein, "organic pigment" is understood to mean any pigment which corresponds to the definition of Ullmann's Encyclopaedia in the "Organic Pigment" chapter. The organic pigment can, for example, be chosen from nitroso, nitro, azo, xanthene, quinoline, anthraquinone or phthalocyanine compounds, compounds of metal complex type, or isoindolinone, isoindoline, quinacridone, perinone, perylene, diketopyrrolopyrrole, thioindigo, dioxazine, triphenylmethane and quinophthalone compounds.

For example, white or colored organic pigments can be chosen from carmine, carbon black, aniline black, azo yellow, quinacridone, phthalocyanine blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, or the pigments obtained by oxidative polymerization of indole or phenol derivatives, such as described in Patent FR 2 679 771.

The pigments in accordance with the disclosure can also be in the form of composite pigments, such as described in Patent EP 1 184 426. These composite pigments can be composed, for example, of particles comprising an inorganic core, at least one binder, which provides for the attachment of the organic pigments to the core, and at least one organic pigment which at least partially covers the core.

The organic pigment can also be a lake. As used herein, "lake" is understood to mean dyes adsorbed onto insoluble particles, the combination thus obtained remaining insoluble during use.

The inorganic substrates onto which the dyes are adsorbed are, for example, alumina, silica, calcium sodium borosilicate, calcium aluminium borosilicate and aluminium.

Mention may be made, for example, among the dyes, of cochineal carmine. Exemplary mention may also be made of the dyes known under the following names: D&C Red 21 (CI 145380), D&C Orange 5 (CI 45370), D&C Red 27 (CI 45410), D&C Orange 10 (CI 45425), D&C Red 3 (CI 45430), D&C Red 4 (CI 15510), D&C Red 33 (CI 17200), FD&C Yellow 5 (CI 19140), FD&C Yellow 6 (CI 15985), D&C Green 5 (CI 61570), D&C Yellow 10 (CI 77002), FD&C Green 3 (CI 42053) or FD&C Blue 1 (CI 42090). Mention may be made, as examples of lakes, of the calcium lakes of D&C Red 7, 11, 31 or 34; the barium lake of D&C Red 12; the strontium lake of D&C Red 13; and the aluminium lakes of FD&C Yellow 5, FD&C Yellow 6, D&C Red 27, D&C Red 21 and FD&C Blue 1.

The pigment can also be a special effect pigment. As used herein, "special effect pigment" is understood to mean a pigment which generally creates a colored appearance (characterized by a certain hue, a certain vividness and a certain lightness) which is not uniform and which changes as a function of the conditions of observation (light, temperature, angles of observation, for example). They thereby contrast with colored pigments, which provide a conventional opaque, semitransparent or transparent uniform color.

There exist several types of special effect pigments, those with a low refractive index, such as fluorescent, photochromic or thermochromic pigments, and those with a greater refractive index, such as pearlescent agents or glitter.

Mention may be made, as examples of special effect pigments, of pearlescent pigments, such as titanium oxide-coated mica covered with iron oxide, mica covered with iron oxide, mica covered with bismuth oxychloride, titanium oxide-coated mica covered with chromium oxide, titanium oxide-coated mica covered with an organic dye, for example of the abovementioned type, and pearlescent pigments based on bismuth oxychloride. They can also be mica particles, at the surface of which at least two successive layers of metal oxides and/or of organic coloring materials are superimposed.

The pearlescent agents can, in one embodiment, have a yellow, pink, red, bronze, orangey, brown, gold and/or coppery color or glint.

Mention may be made, among exemplary pearlescent agents, of pearlescent agents of gold color, for example those sold by Engelhard under the name Gold 222C (CLOISONNE®), SPARKLE GOLD (TIMICA®), GOLD 4504 (CHROMA-LITE®) and MONARCH GOLD 233X (CLOISONNE®); bronze pearlescent agents, for example those sold by Merck under the names BRONZE FINE (17384) (COLORONA®) and BRONZE (17353) (COLORONA®), by Eckart under the name PRESTIGE BRONZE and by Engelhard under the name SUPER BRONZE (CLOISONNE®); orange pearlescent agents, for example those sold by Engelhard under the names ORANGE 363C (CLOISONNE®) and ORANGE MCR 101 (COSMICA) and by Merck under the names PASSION ORANGE (COLORONA®) and MATTE ORANGE (17449) (MICRONA®); brown-colored pearlescent agents, for example those sold by Engelhard under the names NU ANTIQUE COPPER 340XB (CLOISONNE®) and BROWN CL4509 (CHROMALITE®); pearlescent agents with a copper glint, for example those sold by Engelhard under the name COPPER 340A (TIMICA®) and by Eckart under the name PRESTIGE COPPER; pearlescent agents with a red glint sold, for example, by Merck under the name SIENNA FINE (17386) (COLORONA®); pearlescent agents with a yellow glint sold, for example, by Engelhard under the name YELLOW (4502) (CHROMALITE®); red-colored pearlescent agents with a gold glint sold, for example, by Engelhard under the name SUNSTONE G012 (GEMTONE®); black pearlescent agents with a gold glint sold, for example, by Engelhard under the name NU ANTIQUE BRONZE 240 AB (TIMICA®); blue pearlescent agents sold, for example, by Merck under the name MATTE BLUE (17433) (MICRONA®) or DARK BLUE (117324) (COLORONA®); white pearlescent agents with a silvery glint sold, for example, by Merck under the name XIRONA® SILVER; and golden green pinkish orangey pearlescent agents sold, for example, by Merck under the name INDIAN SUMMER (XIRONA®); and mixtures thereof.

In addition to pearlescent agents on a mica support, it is possible to envisage multilayer pigments based on synthetic substrates, such as alumina, silica, calcium sodium borosilicate, calcium aluminium borosilicate and aluminium.

Mention may also be made of pigments with an interference effect which are not attached to a substrate, such as liquid crystals (HELICONES HC from Wacker), or interference holographic glitter (GEOMETRIC PIGMENTS or SPECTRA FIX from Spectratek). Special effect pigments also may comprise fluorescent pigments, whether substances which are fluorescent in daylight or which produce ultraviolet fluorescence, phosphorescent pigments, photochromic pigments, thermochromic pigments and quantum dots, for example sold by Quantum Dots Corporation.

The variety of the pigments which can be used in the present disclosure makes it possible to obtain a rich palette of colors as well as specific optical effects, such as interference, metallic effects.

In one embodiment, the size of the pigment used in the cosmetic composition according to the present disclosure ranges from 10 nm to 200 µm, for example from 100 nm to 80 µm, or from 300 nm to 50 µm or from 500 nm to 20 µm.

In one embodiment, the pigments can be dispersed in the product by virtue of a dispersing agent.

The dispersing agent serves to protect the dispersed particles from the agglomeration or flocculation thereof. This dispersing agent can, for example, be a surfactant, an oligomer, a polymer or a mixture of several of them carrying at least one functionality having a strong affinity for the surface of the particles to be dispersed. In at least one embodiment, they can become attached physically or chemically to the surface of the pigments. These dispersants additionally exhibit at least one functional group compatible with or soluble in the continuous medium. Use may be made, for example, of esters of 12-hydroxystearic acid, and of $C_8$ to $C_{20}$ fatty acid and of polyol, such as glycerol or diglycerol, for example the stearate of poly(12-hydroxystearic acid) with a molecular weight of approximately 750 g/mol, such as that sold under the name of SOLSPERSE® 21000 by Avecia, polyglyceryl-2 dipolyhydroxystearate (CTFA name), sold under the reference DEHYMYLS PGPH by Henkel, or polyhydroxystearic acid, such as that sold under the reference ARLACEL® P100 by Uniqema, and mixtures thereof.

Exemplary mention may be made, as other dispersant which can be used in the compositions of the disclosure, of the quaternary ammonium derivatives of polycondensed fatty acids, such as SOLSPERSE® 17000, sold by Avecia, and polydimethylsiloxane/oxypropylene mixtures, such as those sold by Dow Corning under the references DC2-5185 and DC2-5225 C or by Shin-Etsu under the reference KF6017.

The pigments capable of being used in the cosmetic composition according to the disclosure can be surface-treated with at least one organic agent. These surface treated pigments are pigments which have been completely or partially subjected to a surface treatment of chemical, electronic, electrochemical, mechanochemical or mechanical nature with an organic agent, such as those which are described, for example, in Cosmetics and Toiletries, February 1990, Vol. 105, pp. 53-64, before being dispersed in the composition according to the disclosure. These organic agents can, for example, be chosen from amino acids; waxes, for example carnauba wax and beeswax; fatty acids, fatty alcohols and their derivatives, such as stearic acid, hydroxystearic acid, stearyl alcohol, hydroxystearyl alcohol, lauric acid and their derivatives; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and its derivatives; polyethylene; (meth)acrylic polymers, for example polymethyl(meth)acrylates; polymers and copolymers comprising acrylate units; proteins; alkanolamines; silicone compounds, for example silicones, polydimethylsiloxanes, alkoxysilanes, alkylsilanes or siloxysilicates; fluorinated organic compounds, for example perfluoroalkyl ethers; fluorosilicone compounds; and mixtures thereof. The surface-treated pigments may also have undergone at least one surface treatment, for example more than one surface treatment. The surface-treated pigments can be prepared according to surface treatment techniques well known to a person skilled in the art or found as such commercially. For example, the surface-treated pigments can be covered with an organic layer. The organic agent with which the pigments are treated can, for example, be deposited on the pigments by evaporation of solvent, chemical reaction between the molecules of the surface agent or creation of a covalent bond between the surface agent and the pigments. The surface treatment can thus be carried out, for example, by chemical reaction of a surface agent with the surface of the pigments and creation of a covalent bond between the surface agent and the pigments or fillers. This method is described, for example, in U.S. Pat. No. 4,578,266. In at least one embodiment, use is made of an organic agent covalently bonded to the pigments. The at least one agent for the surface treatment is present in an amount ranging from 0.1 to 50% by weight relative to the total weight of the surface-treated pigments, such as from 0.5 to 30% by weight or from 1 to 10% by weight relative to the total weight of the surface-treated pigments. For example, the surface treatments of the pigments can be chosen from:

PEG-silicone treatments, such as the AQ surface treatment marketed by LCW;

chitosan treatments, such as the CTS surface treatment marketed by LCW;

triethoxycaprylylsilane treatments, such as the AS surface treatment marketed by LCW;

methicone treatments, such as the SI surface treatment marketed by LCW;

dimethicone treatments, such as the COVASIL 3.05 surface treatment marketed by LCW;

dimethicone/trimethylsiloxysilicate treatments, such as the COVASIL 4.05 surface treatment marketed by LCW;

lauroyl lysine treatments, such as the LL surface treatment marketed by LCW;

perfluoropolymethylisopropyl ether treatments, such as the FHC surface treatment marketed by LCW;

disodium stearoyl glutamate treatments, such as the NAI surface treatment marketed by Miyoshi;

perfluoroalkyl phosphate treatments, such as the PF surface treatment marketed by Daito;

acrylate/dimethicone copolymer and perfluoroalkyl phosphate treatments, such as the FSA surface treatment marketed by Daito;

octyltriethylsilane treatments, such as the OTS surface treatment marketed by Daito;

acrylate/dimethicone copolymer treatments, such as the ASC surface treatment marketed by Daito;

isopropyl titanium triisostearate treatments, such as the ITT surface treatment marketed by Daito;

microcrystalline cellulose and carboxymethyl cellulose treatments, such as the AC surface treatment marketed by Daito; and acrylate copolymer treatments, such as the APD surface treatment marketed by Daito.

Exemplary mention may be made, among dyes capable of being used, of the synthetic dyes known under the names D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), FD&C Yellow 5 (CI 19 140), FD&C Yellow 6 (CI 15 985), D&C Green 5 (CI 61 570), D&C Yellow 10 (CI 77 002), FD&C Green 3 (CI 42 053) and FD&C Blue 1 (CI 42 090). Exemplary mention may also be made of natural dyes, such as caramel, beetroot juice, copper chlorophyllin, anthocyans, lycopene and β-carotene.

In at least one embodiment, the at least one coloring material in the makeup composition is present in a total amount ranging from 0.001 to 50% by weight relative to the total weight of the composition, such as from 0.01 to 30% by weight, or from 0.025 to 20% by weight.

The makeup composition according to the disclosure can further comprise at least one filler, which can be present in a total amount ranging from 0.01 to 35% by weight relative to the total weight of the composition, for example from 0.1 to 20% by weight relative to the total weight of the composition. Exemplary mention may be made of talc, mica, silica, kaolin, calcium carbonate, barium sulphate, powders formed of Nylon (such as ORGASOL) and of polyethylene, Teflon, starch, boron nitride, microspheres formed of copolymers, such as EXPANCEL (Nobel Industrie), and silicone resin microbeads (TOSPEARL from Toshiba, for example); and mixtures thereof.

The composition according to the disclosure can further comprise a fatty phase present in an amount ranging from 1 to 98% by weight relative to the total weight of the composition, for example from 5 to 95% by weight, or from 10 to 90% by weight relative to the total weight of the composition. This fatty phase can comprise oils, waxes and/or pasty compounds.

The composition according to the disclosure can thus comprise at least one oil, which can be chosen from hydrocarbon oils, silicone oils, fluorinated oils and mixtures thereof. The oils can be of animal, vegetable, mineral or synthetic origin. The oils can be volatile or nonvolatile. As used herein, "oil" is understood to mean any fatty substance in the liquid form at ambient temperature (20-25° C.) and at atmospheric pressure.

As used herein, "volatile oil" is understood to mean, within the meaning of the disclosure, any oil capable of evaporating on contact with keratinous substances in less than one hour, at ambient temperature and atmospheric pressure. Volatile oils may, for example, have a nonzero vapor pressure, at ambient temperature and atmospheric pressure, ranging from 0.13 Pa to 40,000 Pa, for example from 1.3 Pa to 13,000 Pa, or for example from 1.3 Pa to 1,300 Pa.

As used herein, "silicone oil" is understood to mean an oil comprising at least one silicon atom, for example comprising at least one Si—O group.

As used herein, "fluorinated oil" is understood to mean an oil comprising at least one fluorine atom.

As used herein, "hydrocarbon oil" is understood to mean an oil comprising mainly hydrogen and carbon atoms.

The at least one oil can optionally comprise oxygen, nitrogen, sulphur and/or phosphorus atoms, for example in the form of hydroxyl or acid radicals.

The at least one volatile oil can be chosen from hydrocarbon oils having from 8 to 16 carbon atoms, such as branched $C_8$-$C_{16}$ alkanes (also known as isoparaffins), such as isododecane, isodecane or isohexadecane.

The at least one volatile hydrocarbon oil can also be a volatile linear alkane comprising from 7 to 17 carbon atoms, such as from 9 to 15 carbon atoms or for example from 11 to 13 carbon atoms. Mention may be made, for example, of n-nonadecane, n-decane, n-undecane, n-dodecane, n-tridecane, n-tetradecane, n-pentadecane, n-hexadecane and mixtures thereof.

Use may also be made, as volatile oils, of volatile silicones, for example volatile linear or cyclic silicone oils, such as those having a viscosity of less than or equal to 8 centistokes ($8 \times 10^{-6}$ m$^2$/s) and having, for example, from 2 to 10 silicon atoms, such as from 2 to 7 silicon atoms, these silicones optionally comprising alkyl or alkoxy groups having from 1 to 10 carbon atoms. Exemplary mention may be made of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

Exemplary mention may also be made, as nonvolatile oil, of:

hydrocarbon oils of animal origin, hydrocarbon oils of vegetable origin, such as phytosteryl esters, for example phytosteryl oleate, phytosteryl isostearate and octyidodecyl/phytosteryl lauroyl glutamate; triglycerides composed of esters of fatty acids and of glycerol, for example, the fatty acids of which can have chain lengths ranging from $C_4$ to $C_{36}$ such as from $C_{18}$ to $C_{36}$, it being possible for these oils to be linear or branched and saturated or unsaturated; these oils can, for example, be heptanoic or octanoic triglycerides, shea oil, alfalfa oil, poppy oil, Hokkaido squash oil, millet oil, barley oil, quinoa oil, rye oil, candlenut oil, passionflower oil, shea butter, aloe oil, sweet almond oil, peach kernel oil, peanut oil, argan oil, avocado oil, baobab oil, borage oil, broccoli oil, calendula oil, camelina oil, carrot oil, safflower oil, hemp oil, rapeseed oil, cottonseed oil, coconut oil, cucumber seed oil, wheat germ oil, jojoba oil, lily oil, macadamia oil, maize oil, meadowfoam oil, Saint John's wort oil, monoi oil, hazelnut oil, apricot kernel oil, walnut oil, olive oil, evening primrose oil, palm oil, blackcurrant seed oil, kiwi seed oil, grape seed oil, pistachio oil, pumpkinseed oil, musk rose oil, sesame oil, soya bean oil, sunflower oil, castor oil and watermelon oil, and their mixtures, or triglycerides of caprylic/capric acids, such as those sold by Stéarineries Dubois or those sold under the names MIGLYOL 810®, 812® and 818® by Dynamit Nobel, synthetic ethers having from 10 to 40 carbon atoms, synthetic esters, such as oils of formula $R_1COOR_2$, wherein $R_1$ represents a residue of a linear or branched fatty acid comprising from 1 to 40 carbon atoms and $R_2$ represents a hydrocarbon chain, such as a branched hydrocarbon chain, comprising from 1 to 40 carbon atoms, provided that $R_1+R_2$ is greater than or equal to 10. The esters can be chosen, for example, from fatty acid and alcohol esters, such as, for example, cetearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, hydroxylated esters, such as isostearyl lactate or octyl hydroxystearate, diisopropyl adipate, heptanoates, such as isostearyl heptanoate, octanoates, decanoates or ricinoleates of alcohols or polyalcohols, such as propylene glycol dioctanoate, cetyl octanoate, tridecyl octanoate, 2-ethylhexyl palmitate and 4-diheptanoate, alkyl benzoate, polyethylene glycol diheptanoate, propylene glycol di(2-ethylhexanoate) and their mixtures, benzoates of $C_{12}$-$C_{15}$ alcohols, hexyl laurate, esters of neopentanoic acid, such as isodecyl neopentanoate, isotridecyl neopentanoate, isostearyl neopentanoate or octyldodecyl neopentanoate, esters of isononanoic acid, such as isononyl isononanoate, isotridecyl isononanoate or octyl isononanoate, or hydroxylated esters, such as isostearyl lactate or diisostearyl malate, esters of polyols and esters of pentaerythritol, such as dipentaerythritol tetrahydroxystearate/tetraisostearate, esters of dimer diols and of dimer diacids, copolymers of dimer diol and of dimer diacid and their esters, such as dimer dilinoleyl diol/dimer dilinoleic copolymers and their esters, copolymers of polyols and dimer diacids, and their esters, fatty alcohols comprising a branched and/or unsaturated carbon chain having from 12 to 26 carbon atoms which are liquid at ambient temperature, such as 2-octyldodecanol, isostearyl alcohol, oleyl alcohol, 2-hexyldecanol, 2-butyloctanol and 2-undecylpentadecanal, higher $C_{12}$-$C_{22}$ fatty acids, such as oleic acid, linoleic acid, linolenic acid and their mixtures, dialkyl carbonates, it being possible for the 2 alkyl chains to be identical or different, such as dicaprylyl carbonate, oils with a molar mass ranging from 400 to 10,000 g/mol, for example ranging from 650 to 10,000 g/mol, or for example 750 to 7,500 g/mol or from 1,000 to 5,000 g/mol; mention may be made, for example, of (i) lipophilic polymers, such as polybutylenes, polyisobutylenes, for example hydrogenated, polydecenes and hydrogenated polydecenes, vinylpyrrolidone copolymers, such as the vinylpyrrolidone/1-hexadecene copolymer, polyvinylpyrrolidone (PVP) copolymers, such as copolymers of a $C_2$-$C_{30}$ alkene, such as a $C_3$-$C_{22}$ alkene, and combinations thereof; (ii) esters of linear fatty acids having a total carbon number ranging from 35 to 70, such as pentaerythrityl tetrapelargonate; (iii) hydroxylated esters, such as polyglycerol-2 triisostearate; (iv) aromatic esters, such as tridecyl trimellitate; (v) esters of fatty alcohols or of fatty acids which are branched and comprise from 24 to 28 carbon atoms, such as those described in U.S. Pat. No. 6,491,927, and pentaerythritol esters, such as triisoarachidyl citrate, pentaerythrityl tetraisononanoate, glyceryl triisostearate, glyceryl tri(2-decyltetradecanoate), pentaerythrityl tetraisostearate, polyglyceryl-2 tetraisostearate or pentaerythrityl tetra(2-decyltetradecanoate); (vi) esters and polyesters of dimer diol, such as esters of dimer diol and of fatty acid, and esters of dimer diols and of diacid; (vii) silicone oils, such as nonvolatile polydimethylsiloxanes (PDMSs), PDMSs comprising pendant alkyl or alkoxy groups and/or alkyl or alkoxy groups at the silicone chain ends, which groups each have from 2 to 24 carbon atoms, phenylated silicones such as phenyl trimethicones, phenyl dimethicones, phenyl(trimethylsiloxy)diphenylsiloxanes, diphenyl dimethicones, diphenyl(methyldiphenyl)trisiloxanes and (2-phenylethyl)trimethylsiloxysilicates, dimethicones or phenyl trimethicones with a viscosity of less than or equal to 100 cSt; and (viii) mixtures thereof.

In at least one embodiment, the at least one oil is present in the makeup composition according to the disclosure in an amount ranging from 1 to 90% by weight relative to the total weight of the composition, such as from 2 to 75% by weight or from 3 to 60% by weight, relative to the total weight of the composition.

The composition according to the disclosure can also further comprise at least one wax and/or at least one pasty substance. In at least one embodiment, the at least one wax is present in the makeup composition in a total amount ranging from 0.5 to 30% by weight relative to the total weight of the composition, for example from 1 to 20% by weight, or for example from 2 to 15% by weight relative to the total weight of the composition. In another embodiment, the at least one pasty substance is present in the makeup composition in a total amount ranging from 0.5 to 50% by weight, for example from 1 to 40% by weight, or from 2 to 30% by weight relative to the total weight of the composition.

As used herein, "wax" is understood to mean a lipophilic compound which is solid at ambient temperature (25° C.), which exhibits a reversible solid/liquid change in state and which has a melting point of greater than or equal to 30° C. which can range up to 200° C. The waxes can be chosen from waxes of animal, vegetable, mineral or synthetic origin and mixtures thereof. Mention may be made, for example, of hydrocarbon waxes, such as beeswax, lanolin wax and Chinese insect waxes; rice bran wax, carnauba wax, candelilla wax, ouricury wax, esparto wax, berry wax, shellac wax, Japan wax and sumach wax; montan wax, orange and lemon waxes, microcrystalline waxes, paraffin waxes and ozokerite; polyethylene waxes, the waxes obtained by the Fischer-Tropsch synthesis and waxy copolymers, and also their esters. Exemplary mention may also be made of waxes obtained by catalytic hydrogenation of animal or vegetable oils having linear or branched $C_8$-$C_{32}$ fatty chains. Exemplary mention further be made, among these, of hydrogenated sunflower oil, hydrogenated castor oil, hydrogenated coconut oil, hydrogenated lanolin oil and di(1,1,1-trimethylolpropane) tetrastearate. Exemplary mention may also be made of silicone waxes or fluorinated waxes. For example, use may also be made of the waxes obtained by hydrogenation of castor oil esterified with cetyl alcohol.

As used herein, "pasty substance" is understood to mean a lipophilic fatty compound which exhibits a reversible solid/liquid change in state and which comprises, at a temperature of 23° C., a liquid fraction and a solid fraction. In at least one embodiment, the at least one pasty substance has a hardness at 20° C. ranging from 0.001 to 0.5 MPa, for example from 0.002 to 0.4 MPa. The at least one pasty substance can be chosen from synthetic compounds and compounds of vegetable origin. In at least one embodiment, the at least one pasty substance is obtained by synthesis from starting materials of vegetable origin. Exemplary mention may be made of:

lanolin and its derivatives, such as lanolin alcohol, oxyethylenated lanolins, acetylated lanolin, lanolin esters, such as isopropyl lanolate, or oxypropylenated lanolins, polymeric or nonpolymeric silicone compounds, such as polydimethylsiloxanes with high molecular weights or polydimethylsiloxanes comprising side chains of the alkyl or alkoxy type having from 8 to 24 carbon atoms, such as stearyl dimethicones, polymeric or nonpolymeric fluorinated compounds, vinyl polymers, for example homopolymers of olefins; copolymers of olefins; homopolymers and copolymers of hydrogenated dienes; linear or branched oligomers which are homo- or copolymers of alkyl(meth)acrylates for example those having a $C_8$-$C_{30}$ alkyl group; oligomers which are homo- and copolymers of vinyl esters having $C_8$-$C_{30}$ alkyl groups; or oligomers which are homo- and copolymers of vinyl ethers having $C_8$-$C_{30}$ alkyl groups;

fat-soluble polyethers resulting from the polyetherification between at least one $C_2$-$C_{100}$, for example $C_2$-$C_{80}$, diol; such as copolymers of ethylene oxide and/or of propylene oxide with long-chain $C_6$-$C_{30}$ alkylene oxides, for example such that the ratio by weight of the ethylene oxide and/or propylene oxide to alkylene oxides in the copolymer ranges from 5:95 to 70:30;

polyol ethers chosen from ethers of pentaerythritol and of polyalkylene glycol, ethers of fatty alcohol and of sugar; the ether of pentaerythritol and of polyethylene glycol comprising 5 ethylene oxide (5 EO) units (CTFA name: PEG-5 Pentaerythrityl Ether); the ether of pentaerythritol and of polypropylene glycol comprising 5 propylene oxide (5 PO) units (CTFA name: PPG-5 Pentaerythrityl Ether); and mixtures thereof;

esters and polyesters, such as (i) esters of an oligomeric glycerol, for example esters of diglycerol, such as condensates of adipic acid and of diglycerol, for which a portion of the hydroxyl groups of the glycerols has reacted with a mixture of fatty acids, such as stearic acid, capric acid, stearic acid and isostearic acid, and 12-hydroxystearic acid; (ii) phytosterol esters; (iii) pentaerythritol esters; (iv) esters formed from at least one alcohol, at least one of the alcohols being a Guerbet alcohol, and from a dimer diacid formed from at least one unsaturated fatty acid; (v) noncrosslinked polyesters resulting from the polycondensation between a linear or branched $C_4$-$C_{50}$ dicarboxylic acid or polycarboxylic acid and a $C_2$-$C_{50}$ diol or polyol; (vi) polyesters which result from the esterification, by a polycarboxylic acid, of an aliphatic hydroxycarboxylic acid ester; (vii) ester aliphatic esters resulting from the esterification of an aliphatic hydroxycarboxylic acid ester by an aliphatic carboxylic acid for example comprising from 4 to 30 carbon atoms. In at least one embodiment, the aliphatic hydroxycarboxylic acid ester results from a hydroxylated aliphatic carboxylic acid comprising from 2 to 40 carbon atoms and from 1 to 20 hydroxyl groups; (viii) ester aliphatic esters chosen from the ester resulting from the esterification reaction of hydrogenated castor oil with isostearic acid (mono-, di- or triisostearate of hydrogenated castor oil); and mixtures thereof.

The at least one pasty substance can also be of vegetable origin. Mention may be made, for example, of isomerized jojoba oil, such as trans-isomerized partially hydrogenated jojoba oil, orange wax, shea butter, partially hydrogenated olive oil, cocoa butter or mango oil.

The composition according to the disclosure can also comprise an aqueous phase present in an amount ranging from 1 to 80% by weight relative to the total weight of the composition, such as from 2 to 70% by weight, or from 3 to 60% by weight relative to the total weight of the composition. In another embodiment, this aqueous phase can be composed essentially of water or can comprise a mixture of water and of at least one water-miscible solvent (miscibility in water of greater than 50% by weight at 25° C.) chosen, for example from monoalcohols having from 1 to 5 carbon atoms, such as ethanol or isopropanol, glycols having from 2 to 8 carbon atoms, such as propylene glycol, ethylene glycol, 1,3-butylene glycol or dipropylene glycol, $C_3$-$C_4$ ketones, $C_2$-$C_4$ aldehydes and their mixtures.

The composition according to the disclosure can also comprise at least one surfactant which can be present in a total amount ranging from 0.1 to 10% by weight relative to the total weight of the composition, for example from 0.5 to 8% by weight, or from 1 to 6% by weight relative to the total weight of the composition. The surfactant can be chosen from amphoteric, anionic, cationic or nonionic surface-active agents, such as nonionic surface-active agents. Mention may be made, for example, of:

a) nonionic surface-active agents with an HLB of less than 8 at 25° C., optionally in combination with at least one nonionic surface-active agent with an HLB of greater than 8 at 25° C., for example:

monosaccharide esters and ethers, such as sucrose stearates, sucrose cocoate, sorbitan stearate and mixtures thereof;

esters of fatty acids, such as $C_8$-$C_{24}$ and, for example $C_{16}$-$C_{22}$ fatty acids, and of polyols, for example glycerol or of sorbitol, such as glyceryl stearate, glyceryl laurate, polyglyceryl-2 stearate, sorbitan tristearate and glyceryl ricinoleate;

lecithins, such as soya bean lecithins;

oxyethylenated and/or oxypropylenated ethers (which can comprise from 1 to 150 ethylene oxide and/or propylene oxide groups) of fatty alcohols (such as $C_8$-$C_{24}$ and, such as $C_{12}$-$C_{18}$ alcohols), such as the oxyethylenated ether of stearyl alcohol comprising 2 ethylene oxide units (CTFA name: Steareth-2);

silicone surfactants, such as dimethicone copolyols and alkyl dimethicone copolyols, for example the cyclomethicone/dimethicone copolyol mixture sold under the name Q2-3225C® by Dow Corning;

b) nonionic surface-active agents with an HLB of greater than or equal to 8 at 25° C., for example:

monosaccharide esters and ethers, such as the mixture of cetearyl glucoside and of cetyl and stearyl alcohols, for example MONTANOV 68 from Seppic;

oxyethylenated and/or oxypropylenated glycerol ethers which can comprise from 1 to 150 ethylene oxide and/or propylene oxide units;

oxyethylenated and/or oxypropylenated ethers (which can comprise from 1 to 150 ethylene oxide and/or propylene oxide units) of fatty alcohols, such as $C_8$-$C_{24}$ and such as $C_{12}$-$C_{18}$ fatty alcohols, such as the oxyethylenated ether of stearyl alcohol comprising 20 ethylene oxide units (CTFA name: Steareth-20), the oxyethylenated ether of cetearyl alcohol comprising 30 ethylene oxide units (Ceteareth-30) and the oxyethylenated ether of the mixture of $C_{12}$-$C_{15}$ fatty alcohols comprising 7 ethylene oxide units ($C_{12-15}$ Pareth-7);

esters of fatty acids, such as $C_8$-$C_{24}$ and such as $C_{16}$-$C_{22}$ fatty acids, and of polyethylene glycol (or PEG) (which can comprise from 1 to 150 ethylene oxide units), such as PEG-50 stearate and PEG-40 monostearate;

esters of fatty acids, such as $C_8$-$C_{24}$ and such as $C_{16}$-$C_{22}$ fatty acids, and of oxyethylenated and/or oxypropylenated glycerol ethers (which can comprise from 1 to 150 ethylene oxide and/or propylene oxide units), such as polyoxyethylenated glyceryl monostearate comprising 200 ethylene oxide units, polyoxyethylenated glyceryl stearate comprising 30 ethylene oxide units, polyoxyethylenated glyceryl oleate comprising 30 ethylene oxide units, polyoxyethylenated glyceryl cocoate comprising 30 ethylene oxide units, polyoxyethylenated glyceryl isostearate comprising 30 ethylene oxide units and polyoxyethylenated glyceryl laurate comprising 30 ethylene oxide units;

esters of fatty acids, such as $C_8$-$C_{24}$ and such as $C_{16}$-$C_{22}$ fatty acids, and of oxyethylenated and/or oxypropylenated sorbitol ethers (which can comprise from 1 to 150 ethylene oxide and/or propylene oxide units), such as polysorbate 20 and polysorbate 60;

dimethicone copolyol, such as Q2-5220® from Dow Corning;

dimethicone copolyol benzoate, such as FINSOLV SLB 101® and 201® from Finetex;

propylene oxide and ethylene oxide copolymers, also known as EO/PO polycondensates, which are copolymers composed of polyethylene glycol and polypropylene glycol blocks, such as, for example, polyethylene glycol/polypropylene glycol/polyethylene glycol triblock polycondensates;

c) anionic surfactants, such as:

salts of $C_{16}$-$C_{30}$ fatty acids, for example amine salts, such as triethanolamine stearate or 2-amino-2-methylpropane-1,3-diol stearate;

salts of polyoxyethylenated fatty acids, for example amine salts or alkali metal salts, and mixtures thereof;

phosphoric esters and salts thereof, such as "DEA oleth-10 phosphate" (CRODAFOS N 10N from Croda) or monopotassium monocetyl phosphate;

sulphosuccinates, such as "Disodium PEG-5 citrate lauryl sulfosuccinate" and "Disodium ricinoleamido MEA sulfosuccinate";

alkyl ether sulphates, such as sodium lauryl ether sulphate;

isethionates;

acylglutamates, such as "Disodium hydrogenated tallow glutamate" (AMISOFT HS-21 R® from Ajinomoto) and sodium stearoyl glutamate (AMISOFT HS-11 PF® from Ajinomoto);

soya bean derivatives, such as potassium soyate;

citrates, such as glyceryl stearate citrate;

proline derivatives, such as sodium palmitoyl proline or the mixture of sodium palmitoyl sarcosinate, magnesium palmitoyl glutamate, palmitic acid and palmitoyl proline (SEPIFEEL ONE from Seppic);

lactylates, such as sodium stearoyl lactylate;

sarcosinates, such as sodium palmitoyl sarcosinate or the 75/25 mixture of stearoyl sarcosine and myristoyl sarcosine;

sulphonates, such as sodium $C_{14-17}$ sec alkyl sulphonate;

glycinates, such as sodium cocoyl glycinate;

d) cationic surfactants, such as:

alkylimidazolidiniums, such as isostearyl ethylimidonium ethosulphate;

ammonium salts, such as ($C_{12-30}$ alkyl)tri($C_{1-4}$ alkyl) ammonium halides, such as N,N,N-trimethyl-1-docosanaminium chloride (or behentrimonium chloride);

e) amphoteric surfactants, such as N-acylamino acids, for example N-alkylaminoacetates and disodium cocoamphodiacetate, and amine oxides, such as stearamine oxide;

f) and mixtures thereof.

The makeup composition according to the disclosure can further comprise at least one agent normally used in cosmetics chosen, for example, from reducing agents, softeners, antifoaming agents, moisturizing agents, UV screening agents, ceramides, cosmetic active principles, peptizing agents, fragrances, proteins, vitamins, propellents, hydrophilic or lipophilic polymers which are or are not able to form a film, or lipophilic or hydrophilic gelling agents. The above additives are generally present in an amount ranging from 0.01% to 10% by weight, for each of them, with respect to the total weight of the composition. Of course, a person skilled in the art will take care to choose the constituents of the composition so that the advantageous properties attached to the invention are not, or not substantially, detrimentally affected.

The makeup composition according to the disclosure can be provided in a form chosen from a suspension, a dispersion, a solution, a gel, an emulsion, such as an oil-in-water (O/W), water-in-oil (W/O) or multiple (W/O/W or polyol/O/W or O/W/O) emulsion, a cream, a foam, a stick, a dispersion of vesicles, for example of ionic or nonionic lipids, a two-phase or multiphase lotion, a spray, a powder and a paste.

A person skilled in the art can choose the appropriate formulation form and its method of preparation on the basis of his general knowledge, taking into account, on the one hand, the nature of the constituents used, such as their solubility in the carrier, and, on the other hand, the application envisaged for the composition.

In at least one embodiment of the present disclosure, the composition is in the form of an emulsion, such as an oil-in-water or water-in-oil or multiple emulsion, for example a water-in-oil emulsion. In another embodiment, the composition comprises:

at least one aqueous phase in an amount ranging from 1 to 80% relative to the total weight of the composition, which can optionally further comprise additives such as polyols, salts, active principles or hydrophilic polymers, at least one surfactant in an amount ranging from 0.1 to 10% relative to the total weight of the composition, such as at least one nonionic surfactant, at least one fatty phase in an amount ranging from 1 to 90% relative to the total weight of the composition, which can optionally further comprise waxes, pasty substances, active principles and/or fragrances, at least one coloring material in an amount ranging from 5 to 20% relative to the total weight of the composition, at least one filler in an amount ranging from 0.1 to 20% relative to the total weight of the composition, and at least one supramolecular polymer as disclosed herein in an amount ranging from 0.1 to 10% relative to the total weight of the composition.

In at least one embodiment, the composition in the emulsion form is a foundation.

In another embodiment, the composition is anhydrous and can, for example, be provided in the form of a stick. In a further embodiment, the composition comprises:

at least one coloring material present in an amount ranging from 1 to 20% relative to the total weight of the composition, at least one wax present in an amount ranging from 1 to 50% relative to the total weight of the composition at least one pasty substance in an amount ranging from 1 to 30% relative to the total weight of the composition, at least one oil present in an amount ranging from 1 to 60% relative to the total weight of the composition, at least one filler present in an amount ranging from 0.1 to 10% relative to the total weight of the composition, at least one supramolecular polymer as disclosed herein present in an amount ranging from 0.1 to 70% relative to the total weight of the composition.

In at least one embodiment, the composition in the form of a stick is a lipstick.

The composition according to the disclosure is provided in the form of a composition for making up the skin and/or lips, such as the skin of the face or body; it can be a product for the complexion, such as a foundation, a face powder or an eyeshadow; a product for the lips, such as a lipstick or a lipcare product; a concealer; a blusher; an eyeliner; a lip or eye pencil; a product for making up the body; or a gloss (lip gloss).

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

Method for Measuring the Transfer Index

A.

The transfer index in the presence of sebum of the deposited layer obtained with a composition was determined according to the measurement protocol described below.

A substrate (square of 40 mm×40 mm) composed of a layer of neoprene foam which was adhesive on one of its faces (sold under the name RE40X70 RE70X40 212B from Joint Technique Lyonnais Ind.) was prepared. An adhesive ring having an internal diameter of 24 mm and a thickness of 250 μm was fixed to the nonadhesive face of the substrate. The composition was applied inside the ring and was levelled with a glass slide, in order to obtain a deposited layer of the composition with a thickness of 250 μm, then the ring was removed and drying was allowed to take place in an oven at 37° C. for 20 hours.

The substrate was subsequently adhesively bonded, via its adhesive face, to an endpiece with a diameter of 27 mm fixed to a press (STATIF MANUEL SV-1 from Imada Co. Ltd) equipped with a tensile testing machine (DPS-5R from Imada Co. Ltd).

A strip with a width of 4 cm and a length of 21 cm was drawn on a photographic grade coated paper (reference Epson S041061 of 102 g/m$^2$); 5 compartments, each having a length of 4.2 cm, were drawn in this strip along the longitudinal axis of the strip. The paper was placed on the bed of the press.

A drop of 10 μl of artificial sebum having the following composition:

| | |
|---|---|
| triolein | 29% |
| oleic acid | 28.5% |
| oleyl oleate | 18.5% |
| squalene | 14% |
| cholesterol | 7% |
| cholesterol palmitate | 3% | was deposited at the center of the first compartment.

The substrate (comprising the sample of composition) was then pressed onto the first compartment of the paper strip at a force of 4 kg exerted for 5 seconds. The paper was displaced in a rectilinear and uniform manner over the entire length of the strip, so that the substrate was in contact with the entire length of the strip. The rate of displacement of the strip was of the order of 10 cm/s.

The trail of product deposited on the paper strip was observed visually. A grade ranging respectively from 0.5 to 5, in increments of 0.5, was assigned according to the number of compartments, from the first to the fifth, traversed, in all or part, by the possible trail of product.

Grade 5 was assigned in the case where the trail of product reached the end of the fifth compartment or beyond.

Grade 5 was also assigned when, by observation, after having performed the relative displacement between the paper and substrate, substantially no product (less than 10%) remained on the substrate. In the latter case, the transfer may be described as total.

Grade 5 was also assigned when the trail of product extended beyond the fifth compartment, independently of the amount of product remaining on the substrate.

Grade 0 was assigned in the case where no product present on the substrate had transferred onto the paper strip. In this case, no visible trace could be observed on the sheet. The transfer may be described as zero.

By convention, the line of separation between compartment n and compartment n+1 formed part of compartment n.

The way in which the other grades were assigned according to the spot on compartments 1 to 5 where the trail of product stops is illustrated in the table below. For these grades, a greater or lesser amount of product remained on the substrate. The transfer may be described as partial.

| No. of the compartment where the trail of product stopped | Grade | |
|---|---|---|
| | Beyond half the compartment | At most at half the compartment |
| 5 | 4.5 | |
| | | 4 |
| 4 | 3.5 | |
| | | 3 |
| 3 | 2.5 | |
| | | 2 |

| No. of the compartment where the trail of product stopped | Grade | |
|---|---|---|
| | Beyond half the compartment | At most at half the compartment |
| 2 | 1.5 | 1 |
| 1 | 0.5 | |

B.

The transfer index in the presence of sweat of the deposited layer obtained with a composition was determined according to the same measurement protocol, the drop of 10 μl artificial sebum being replaced with a drop of 10 μl of artificial sweat having the following composition:

| | |
|---|---|
| lactic acid | 0.1142% |
| ammonia | 0.1764% |
| glycine | 0.00758% |
| serine | 0.0214% |
| urea | 0.051% |
| sodium chloride | 0.07949% |
| pure water | q.s. for 100% |

EXAMPLE 1

Synthesis of Polymer 1 According to the Present Disclosure 100 g of dihydroxylated hydrogenated poly(1,2-butadiene) polymer (GI3000 from Nisso; Mn=3100) were dried at 80° C. under reduced pressure overnight. This polymer was dissolved in 400 ml of anhydrous toluene. 25 μl of catalyst (dibutyltin dilaurate) was added and heating was carried out at 80° C. with stirring until a homogeneous solution was obtained. 15 g of isocyanate-functionalized molecule with the following structure:

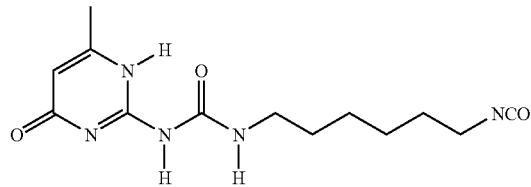

in solution in 300 ml of anhydrous toluene, was added under a controlled atmosphere at 40° C. The reaction mixture was heated to 100° C. and then stirred at this temperature for 4 hours. The reaction was monitored by infrared spectroscopy, with monitoring of the complete disappearance of the peak characteristic of the isocyanates at 2260 cm$^{-1}$. At the end of the reaction, 100 ml of ethanol was added, in order to remove any trace of residual isocyanate, and then the mixture was filtered after having added isododecane in order to render the solution less viscous. The polymer solution was then directly stripped with isododecane.

A solution of the final polymer in isododecane, at a solids content of 21%, was obtained; the polymer was characterized by GPC (Mn=6400 and polydispersity index=1.85) and $^{1}$H NMR (spectrum in accordance with what was expected).

EXAMPLE 2

Synthesis of Polymer 2 According to the Present Disclosure 106.1 g of dihydroxylated hydrogenated poly(1,2-butadiene) polymer (GI2000 from Nisso, Mn=2100) was heated at 80° C. under reduced pressure for 2 hours in the presence of 22 mg of catalyst (dibutyltin dilaurate). The temperature of the mixture was brought down to 20° C. under argon, followed by the addition of 10 ml of isododecane and 19.3 g of isophorone diisocyanate (IPDI). The mixture was stirred at 20° C. for 16 hours under a controlled atmosphere and was then heated to 120° C., followed by the addition of 25 ml of propylene carbonate. 12 g of 6-methylisocytosine were added, resulting in a homogeneous white suspension. This suspension was heated to 140° C. and was stirred at this temperature for 6 hours. The reaction was monitored by infrared spectroscopy until the peak characteristic of the isocyanates (2250 cm$^{-1}$) had completely disappeared. The mixture was subsequently brought back down to 30° C. and 400 ml of heptane, 200 ml of THF and 50 ml of ethanol were added thereto, before filtering through celite. The mixture was then stripped with isododecane.

At the end, a solution of the polymer in isododecane, at a solids content of 20%, was obtained; the polymer was characterized by GPC (Mn=7000 and polydispersity index=2.05).

EXAMPLE 3

Synthesis of Polymer 3 According to the Present Disclosure 99 g of dihydroxylated hydrogenated poly(1,2-butadiene) polymer (GI3000 from Nisso, Mn=3100) was heated at 80° C. under reduced pressure for 2 hours in the presence of 22 mg of catalyst (dibutyltin dilaurate). The temperature of the mixture was brought down to 20° C. under argon, followed by the addition of 30 ml of isododecane and 11 g of isophorone diisocyanate (IPDI). The mixture was stirred at 20° C. for 16 hours under a controlled atmosphere and was then heated to 120° C., followed by the addition of 25 ml of propylene carbonate. 8.1 g of 6-methylisocytosine was added, resulting in a homogeneous white suspension. This suspension was heated to 140° C. and was stirred at this temperature for 6 hours. The reaction was monitored by infrared spectroscopy until the peak characteristic of the isocyanates (2250 cm$^{-1}$) had completely disappeared. The mixture was subsequently brought down again to 30° C. and 1 liter of heptane was added thereto, before filtering through celite. The mixture was then stripped with isododecane.

At the end, a solution of the polymer in isododecane, at a solids content of 20%, was obtained; the polymer was characterized by GPC (Mn=4200 and polydispersity index=2.34).

EXAMPLE 4

Synthesis of Polymer 4 According to the Present Disclosure 89 g of dihydroxylated hydrogenated poly(1,2-butadiene) polymer (GI3000 from Nisso, Mn=3100) were heated at 80° C. under reduced pressure for 2 hours in the presence of 22 mg of catalyst (dibutyltin dilaurate). The temperature of the mixture was brought down to 20° C. under argon, followed by the addition of 60 ml of isododecane and 11.6 g of 4,4'-dicyclohexylmethane diisocyanate. The mixture was stirred at 20° C. for 16 hours under a controlled atmosphere and was then heated to 120° C., followed by the addition of 40 ml of propylene carbonate. 6.64 g of 6-methylisocytosine were added, resulting in a homogeneous white suspension. This suspension was heated to 140° C. and was stirred at this temperature for 8 hours. The reaction was monitored by infrared spectroscopy until the peak characteristic of the isocyanates (2250 cm$^{-1}$) had completely disappeared. The mixture was subsequently brought down again to 30° C. and 250 ml of isododecane and 500 ml of heptane are added thereto, before filtering through celite. The mixture was then stripped with isododecane.

At the end, a solution of the polymer in isododecane, at a solids content of 22%, was obtained; the polymer was characterized by GPC (Mn=10700 and polydispersity index=2.26).

EXAMPLE 5

Synthesis of Polymer 5 According to the Present Disclosure 143.1 g of dihydroxylated hydrogenated poly(1,2-butadiene) polymer (GI2000 from Nisso, Mn=2100) were heated at 80° C. under reduced pressure for 2 hours in the presence of 33 mg of catalyst (dibutyltin dilaurate). The temperature of the mixture was brought down to 20° C. under argon, followed by the addition of 85 ml of isododecane and 30.8 g of 4,4'-dicyclohexylmethane diisocyanate. The mixture was stirred at 20° C. for 16 hours under a controlled atmosphere and was then heated to 120° C., followed by the addition of 70 ml of propylene carbonate. 22.6 g of 6-methylisocytosine was added, resulting in a homogeneous white suspension. This suspension was heated to 140° C. and was stirred at this temperature for 8 hours. The reaction was monitored by infrared spectroscopy until the peak characteristic of the isocyanates (2250 cm$^{-1}$) had completely disappeared. The mixture was subsequently brought down again to 20° C. and 700 ml of isododecane and 500 ml of heptane were added thereto, before filtering through celite. The mixture was then stripped with isododecane.

At the end, a solution of the polymer in isododecane, at a solids content of 20%, was obtained; the polymer was characterized by GPC (Mn=8400 and polydispersity index=2.00).

EXAMPLE 6

Foundation According to the Present Disclosure

A liquid foundation was prepared comprising (% by weight relative to the total weight of the composition):

| Phase A1: | |
|---|---|
| Cetyl PEG/PPG-14/14 dimethicone (ABIL EM 97 from Goldschmidt) | 1.8% |
| Isostearyl diglyceryl succinate | 0.6% |
| Isododecane | 15.5% |
| Cyclopentasiloxane | 5.0% |
| Polymer of Example 1 (at 21% in isododecane) | 10% (i.e. 2.1% on a dry basis) |

| Phase A2: | |
|---|---|
| Cyclopentasiloxane | 5.0% |
| Iron oxides coated with aluminium stearoyl glutamate | 3.2% |
| Titanium dioxide coated with aluminium stearoyl glutamate | 6.8% |
| Phase A3: | |
| Phenylated silicone gum + cyclopentasiloxane (MIRASIL C-DPDM from Blue Star) | 3.0% |
| Phase A4: | |
| Nylon 12 powder | 8.0% |
| Phase B: | |
| Preservative | q.s. |
| Magnesium sulphate | 0.7% |
| Water | q.s. for 100% |

The constituents of phase A1 were weighed into a beaker while stirring with a Moritz mixer at 1500 revolutions/min, the temperature being maintained at ambient temperature (25° C.). Phase A2 was prepared separately by milling the pigments on a triple roll mill and then it was added with stirring to the preceding mixture. Phases A3 and A4 were subsequently added while continuing to stir. To prepare phase B, the water was brought to boiling and then the other constituents of phase B were added. The emulsion was prepared at ambient temperature. The two phases both had a temperature in the vicinity of ambient temperature. The aqueous phase B was poured slowly into the fatty phase, during which the stirring speed of the Moritz mixer was increased up to 4000 revolutions/min. After addition, stirring was allowed to take place for a further 10 minutes at ambient temperature.

A liquid foundation was obtained which exhibited good hold.

EXAMPLE 7

Comparative Foundation

A comparative liquid foundation was prepared which comprised (% by weight relative to the total weight of the composition):

| Phase A1: | |
|---|---|
| Cetyl PEG/PPG-14/14 dimethicone (ABIL EM 97 from Goldschmidt) | 1.8% |
| Isostearyl diglyceryl succinate | 0.6% |
| Isododecane | 15.2% |
| Phase A2: | |
| Cyclopentasiloxane | 5.0% |
| Iron oxides coated with aluminium stearoyl glutamate | 3.2% |
| Titanium dioxide coated with aluminium stearoyl glutamate | 6.8% |
| Phase A3: | |
| Polyurethane* | 15% (i.e., 2.1% on a dry basis) |
| Ethanol | 2.0% |
| Phase A4: | |
| Nylon 12 powder | 8.0% |

-continued

| Phase B: | |
|---|---|
| Preservative | q.s. |
| Magnesium sulphate | 0.7% |
| Water | q.s. for 100% |

*Polyurethane/polyurea/poly(ethylene/butylene) copolymer carrying an ionizable functional group prepared according to Example 5 of EP 1797868, as a 14% solution in isododecane.

The constituents of phase A1 were weighed into a beaker with stirring, the temperature being maintained at ambient temperature. Phase A2 was prepared separately by milling the pigments on a triple roll mill and then it was added with stirring to the preceding mixture. Phase A3 was prepared separately by mixing the polymer with the ethanol with stirring. It was subsequently introduced into the preceding mixture with stirring, the temperature being maintained at ambient temperature. Phase A4 was then added while continuing to stir. To prepare the aqueous phase B, the water was brought to boiling and then the other constituents of phase B were added. The emulsion was prepared at ambient temperature. The two phases both had a temperature in the vicinity of ambient temperature. The aqueous phase B was poured slowly into the fatty phase, during which the stirring speed of the Moritz mixer was increased up to 4000 revolutions/min. After addition, stirring was allowed to take place for a further 10 minutes at ambient temperature. A comparative liquid foundation was obtained.

Measurement of the Freedom from Transfer

The transfer index was measured in the presence of sebum and of sweat for the composition of Example 6 (Inventive) and the above Comparative Composition (Example 7), according to the measurement protocol described above. The following results were obtained:

| | Example 6 (invention) | Comparative Example |
|---|---|---|
| Transfer index - Sweat | 0 | 0.5 |
| Transfer index - Sebum | 1.5 | 3.5 |

It was found that the composition of the invention had a better transfer index, in the presence of sebum or of sweat, than that of the composition of the prior art.

EXAMPLE 8

Lipstick Stick

A lipstick in the form of a stick was prepared which comprised (% by weight relative to the total weight of the composition):

| | % by weight |
|---|---|
| Polyethylene wax | 11.0 |
| Hydrogenated polyisobutene | 5.7 |
| Sucrose acetate isobutyrate | 5.0 |
| $C_{30-50}$ Alcohols | 2.0 |
| Polyhydroxystearic acid | 0.2 |
| Pigments | 3.6 |
| Mica | 1.5 |
| Titanium dioxide | 3.2 |
| Polymer of Example 1 as a 15% solution in isododecane | q.s. for 100% (i.e., 10% on a dry basis) |

Phase A was weighed into a jacketed heating pan and then heating was carried out to 95° C. with stirring. When the mixture had melted and was homogeneous, phase B was incorporated and stirring was allowed to take place for 5 minutes. Phase C was incorporated and then the heating vessel was rapidly covered. Stirring was allowed to take place for 10 minutes and then the mixture was poured into a mould of 8 mm pen type. After cooling, a lipstick stick was obtained.

The composition was tested in vitro according to the push & pull test, which consists in evaluating the resistance of the formulation to water and to oil.

A Blenderme sheet was adhesively bonded to a foam, the assembly was brought to 33° C., the test composition was then applied thereto and the assembly was allowed to dry for 10 minutes. A test specimen was cut out therefrom and the color (L, a, b) (film) thereof was measured using a Chromametre CR200. A control test specimen, without deposition of composition, was prepared and the color (L, a, b) (bare film) thereof was also measured. The test specimen to be tested was put on a tensile testing press, a pressure of 300 g/cm² (or 760 g) was applied and the paper strip was pulled manually over its entire length with a rate of 1 cm/sec. The residual color of the film (L, a, b) (residual) was subsequently measured. The hold was calculated in the following way:

Hold(%)=100×[ΔE(residual/bare film)/ΔE(film/bare film)].

The following result was obtained: hold in vitro: 94.58±0.88%.

It was thus found that the composition according to the invention had good hold properties.

What is claimed is:

1. A method for making up the skin and/or lips, comprising applying to the skin and/or lips at least one cosmetic makeup composition comprising, in a cosmetically acceptable medium, at least one polyalkene-based supramolecular polymer and at least one coloring material, wherein the at least one polyalkene-based supramolecular polymer is chosen from those of the formula:

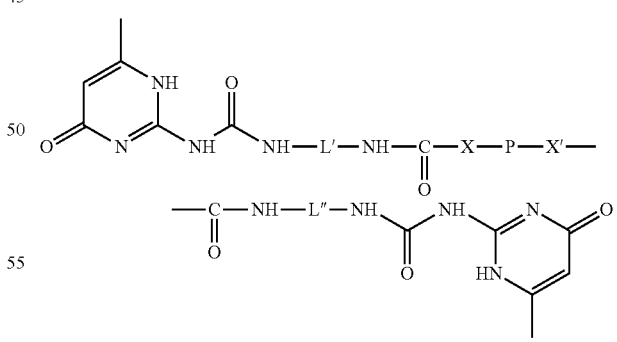

wherein:
L' and L" are chosen from, independently of one another, isophorone or 4,4'-methylenebiscyclohexylene,
X and X' denote O; and
P represents polyethylene, polybutylene, polybutadiene, polyisoprene, poly(1,3-pentadiene), polyisobutylene and copolymers thereof and hydrogenated forms thereof and wherein said cosmetically acceptable medium comprises at least one ingredient chosen from fillers, oils, waxes, pasty substances, water, surfactants, reducing agents, softeners, antifoaming agents, moisturizing agents, UV screening agents, ceramides, cosmetic active principles, peptizing agents, fragrances, proteins, vitamins, propellents, hydrophilic or lipophilic polymers which are or are not able to form a film, and lipophilic or hydrophilic gelling agents.

2. The method according to claim 1, wherein the reaction is a condensation reaction.

3. The method according to claim 1, wherein the at least one polyalkene-based supramotecular polymer is present in the composition in a total amount of 0.1 to 70% by weight relative to the total weight of the composition.

4. The method according to claim 1, wherein the composition is provided in the form of an emulsion comprising:
  at least one aqueous phase in an amount ranging from 1 to 80% by weight relative to the total weight of the composition,
  at least one surfactant in an amount ranging from 0.1 to 10% by weight relative to the total weight of the composition,
  at least one fatty phase in an amount ranging from 1 to 90% by weight relative to the total weight of the composition,
  at least one coloring material in an amount ranging from 5 to 20% by weight relative to the total weight of the composition,
  at least one filler in an amount ranging from 0.1 to 20% by weight relative to the total weight of the composition, and
  the at least one polyalkene-based supramolecular polymer in an amount ranging from 0.1 to 10% by weight relative to the total weight of the composition.

5. The method according to claim 1, in which the composition is anhydrous and comprises:
  at least one coloring material in an amount ranging from 1 to 20% by weight relative to the total weight of the composition,
  at least one wax in an amount ranging from 1 to 50% by weight relative to the total weight of the composition,
  at least one pasty substance in an amount ranging from 1 to 30% by weight relative to the total weight of the composition,
  at least one oil in an amount ranging from 1 to 60% by weight relative to the total weight of the composition,
  at least one filler in an amount ranging from 0.1 to 10% by weight relative to the total weight of the composition, and
    the at least one polyalkene-based supramolecular polymer in an amount ranging from 0.1 to 10% by weight relative to the total weight of the composition.

6. A cosmetic composition for making up the skin and/or lips, comprising, in a cosmetically acceptable medium, at least one polyalkene-based supramolecular polymer and at least one coloring material, wherein the at least one polyalkene-based supramolecutar polymer is chosen from those of the formula:

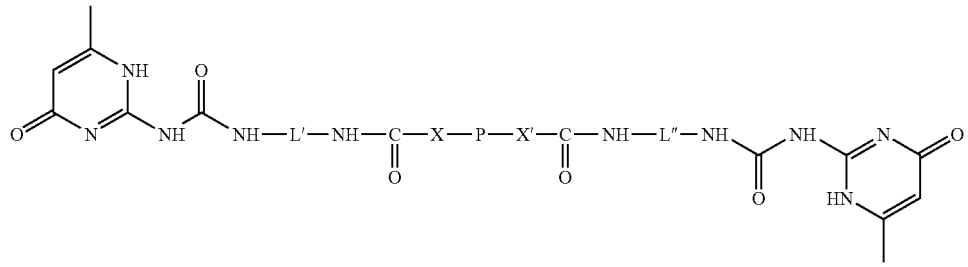

wherein;

L' and L" are chosen from, independently of one another, isophorone 4,4'-methylenebiscyclohexylene, X and X' denote O; and P represents polyethylene, polybutylene, polybutadienk, polyisoprene, poly(1,3-pentadiene), polyisobutyiene and copolymers thereof and hydrogenated forms thereof; and wherein said cosmetically acceptable medium comprises at least one ingredient chosen from fillers, oils, waxes, pasty substances, water, surfactants, reducing agents, softeners, antifoaming agents, moisturizing agents, UV screening agents, ceramides, cosmetic active principles, peptizing agents, fragrances, proteins, vitamins, propellents, hydrophilic or lipophilic polymers which are or are not able to form a film, and lipophilic or hydrophilic gelling agents.

7. The composition according to claim 6, wherein the reaction is a condensation reaction.

8. The composition according to claim 6, wherein the at least one polyalkene-based supramolecular polymer is present in the composition in a total amount of 0.1 to 70% by weight relative to the total weight of the composition.

9. The composition according to claim 6, comprising at least one coloring material present in a total amount ranging from 0.001 to 50% by weight relative to the total weight of the composition.

10. The composition according to claim 6, wherein the composition is provided in the form chosen from foundations, face powders, eyeshadows; products for the lips, concealers; blushers; eyeliners; lip or eye pencils; and products for making up the body.

11. The composition according to claim 7, wherein the composition is in the form of a foundation and wherein the at least one polyalkene-based supramolecular polymer, alone or as a mixture, is present in a total amount of 0.1 to 10% by weight, with respect to the total weight of the composition.

12. The composition according to claim 11, wherein the composition is provided in the form of an emulsion comprising:
  at least one aqueous phase in an amount ranging from 1 to 80% by weight relative to the total weight of the composition,
  at least one surfactant in an amount ranging from 0.1 to 10% by weight relative to the total weight of the composition,
  at least one fatty phase in an amount ranging from 1 to 90% by weight relative to the total weight of the composition, at least one coloring material in an amount ranging from 5 to 20% by weight relative to the total weight of the composition, at least one filler in an amount ranging from 0.1 to 20% by weight relative to the total weight of the composition, and the at least one polyalkene-based supramolecular polymer in an amount ranging from 0.1 to 10% by weight relative to the total weight of the composition.

13. The composition according to claim 6, wherein the composition is in the form of a lipstick and wherein the at least one polyalkene-based supramolecular polymer, alone or as a mixture, is present in a total amount of 0.1 to 70% by weight, with respect to the total weight of the composition.

14. The composition according to claim 13, in which the composition is in the form of an anhydrous composition comprising:

at least one coloring material in an amount ranging from 1 to 20% by weight relative to the total weight of the composition, at least one wax in an amount ranging from 1 to 50% by weight relative to the total weight of the composition, at least one pasty substance in an amount ranging from 1 to 30% by weight relative to the total weight of the composition, at least one oil an amount ranging from 1 to 60% by weight relative to the total weight of the composition, at least one filler in an amount ranging from 0.1 to 10% by weight relative to the total weight of the composition, and the at least one polyalkene-based supramolecular polymer in an amount ranging from 0.1 to 10% by weight relative to the total weight of the composition.

15. The method according to claim 4, wherein the composition is a foundation.

16. The method according to claim 5, wherein the composition is a lipstick.

17. The method according to claim 1, wherein the at least one joining group is capable of forming at least 4 H bonds.

18. The method according to claim 1, wherein the at least one joining group is capable of forming 4 H bonds.

19. The method according to claim 1, wherein P is a poly(ethylene/butylene).

20. The method according to claim 3, wherein the at least one polyalkene-based supramolecular polymer is present in the cosmetic makeup composition in a total amount ranging from 0.5 to 15% by weight relative to the total weight of the composition.

21. The composition according to claim 6, wherein P is a poly(ethylene/butylene).

22. The composition according to claim 8, wherein the at least one polyalkene-based supramolecular polymer is present in the composition in a total amount ranging from 0.5 to 15% by weight relative to the total weight of the composition.

23. The composition according to claim 9, wherein the at least one coloring material is present in a total amount ranging from 0.025 to 20% by weight relative to the total weight of the composition.

24. The composition according to claim 6, wherein P is hydrogenated polybutadiene.

25. The composition according to claim 6, which is comfortable, free from transfer and exhibits good hold properties.

* * * * *